United States Patent
Kim et al.

(10) Patent No.: US 9,775,803 B2
(45) Date of Patent: Oct. 3, 2017

(54) LIPOSOME COMPRISING ELASTIN-LIKE POLYPEPTIDE AND TUMOR CELL TARGETING MATERIAL AND USE THEREOF

(75) Inventors: Min Sang Kim, Anseong-si (KR); Hyun Ryoung Kim, Guri-si (KR); Jae Chan Park, Yongin-si (KR); Su Young Chae, Suwon-si (KR); Sang Joon Park, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 1424 days.

(21) Appl. No.: 13/608,617

(22) Filed: Sep. 10, 2012

(65) Prior Publication Data

US 2013/0102993 A1 Apr. 25, 2013
US 2017/0165198 A9 Jun. 15, 2017

(30) Foreign Application Priority Data

Oct. 19, 2011 (KR) .......... 10-2011-0107055
Feb. 1, 2012 (KR) .......... 10-2012-0010506

(51) Int. Cl.
| | |
|---|---|
| A61K 9/127 | (2006.01) |
| A61K 47/42 | (2017.01) |
| A61M 37/00 | (2006.01) |
| A61K 47/48 | (2006.01) |
| A61K 31/704 | (2006.01) |
| B82Y 5/00 | (2011.01) |

(52) U.S. Cl.
CPC .......... *A61K 9/127* (2013.01); *A61K 9/1271* (2013.01); *A61K 9/1272* (2013.01); *A61K 31/704* (2013.01); *A61K 47/42* (2013.01); *A61K 47/48815* (2013.01); *A61M 37/00* (2013.01); *B82Y 5/00* (2013.01); *Y10S 977/797* (2013.01); *Y10S 977/907* (2013.01)

(58) Field of Classification Search
CPC .... A61K 9/127; A61K 9/1271; A61K 9/1272; A61K 47/42; A61K 47/48815; A61K 47/48823; Y10S 977/907
See application file for complete search history.

(56) References Cited

U.S. PATENT DOCUMENTS

| | | |
|---|---|---|
| 5,720,976 A | 2/1998 | Kim et al. |
| 5,767,071 A | 6/1998 | Palladino et al. |

(Continued)

FOREIGN PATENT DOCUMENTS

| | | |
|---|---|---|
| JP | 1993-228358 A | 2/1992 |
| JP | 2000-143532 A | 5/2000 |

(Continued)

OTHER PUBLICATIONS

Dubey et al. Liposomes Modified with Cyclic RGD Peptide for Tumor Targeting. Journal of Drug Targeting. Jun. 2004, vol. 12, No. 5, pp. 257-264.*

(Continued)

*Primary Examiner* — Jeffrey E Russel
(74) *Attorney, Agent, or Firm* — Leydig, Voit & Mayer, Ltd.

(57) ABSTRACT

A liposome including an elastin-like polypeptide (ELP) and a tumor cell targeting material, a pharmaceutical composition including the liposome, and a method of delivering an active agent to a target site using the liposome.

19 Claims, 12 Drawing Sheets

(56) References Cited

U.S. PATENT DOCUMENTS

| | | | |
|---|---|---|---|
| 5,780,426 | A | 7/1998 | Palladino et al. |
| 5,810,888 | A | 9/1998 | Fenn |
| 5,817,750 | A | 10/1998 | Ruoslahti et al. |
| 5,955,572 | A | 9/1999 | Ruoslahti et al. |
| 6,200,598 | B1 | 3/2001 | Needham |
| 7,029,652 | B2 | 4/2006 | DeNardo et al. |
| 7,202,330 | B2 | 4/2007 | DeJong et al. |
| 7,595,051 | B2 | 9/2009 | Brooks et al. |
| 7,598,341 | B2 | 10/2009 | Hanahan et al. |
| 7,718,190 | B2 | 5/2010 | Keller et al. |
| 2006/0153770 | A1 | 7/2006 | DeNardo et al. |
| 2007/0077230 | A1 | 4/2007 | Mon |
| 2007/0078085 | A1* | 4/2007 | Chung ................ A61K 31/70 514/44 R |
| 2007/0148220 | A1 | 6/2007 | Müller et al. |
| 2008/0213190 | A1 | 9/2008 | Del Gatto et al. |
| 2010/0098748 | A1 | 4/2010 | Wang et al. |
| 2010/0189643 | A1* | 7/2010 | Chilkoti ........... A61K 47/48246 424/1.65 |
| 2011/0039770 | A1* | 2/2011 | Phipps ............. A61K 47/48276 514/6.9 |
| 2012/0171227 | A1* | 7/2012 | Baker, Jr. ......... A61K 47/48246 424/181.1 |
| 2014/0199235 | A1* | 7/2014 | Jeong ................ A61K 49/0067 424/1.37 |
| 2016/0235870 | A1* | 8/2016 | Chong ................ C07D 401/12 |

FOREIGN PATENT DOCUMENTS

| | | |
|---|---|---|
| JP | 2007-515452 A | 6/2007 |
| JP | 2009-269846 A | 11/2009 |
| KR | 2001-0013665 A | 2/2001 |
| KR | 10/0573743 B1 | 11/2005 |
| KR | 10-0570494 B1 | 4/2006 |
| WO | WO 97/08203 A1 | 3/1997 |
| WO | WO 2004/010951 A2 | 2/2004 |
| WO | WO 2008/039188 A1 | 4/2008 |

OTHER PUBLICATIONS

Na et al. Elastin-like polypeptide modified liposomes for enhancing cellular uptake into tumor cells. Biointerfaces. 2012; available online Nov. 2, 2011. vol. 91, pp. 130-136.*

Needham, David, et al., "A New Temperature-sensitive Liposome for Use with Mild Hyperthermia: Characterization and Testing in Human Tumor Xenograft Model," *Cancer Research*, 60, pp. 1197-1201 (2000).

Hauck, Marlene L., et al., "Phase I Trial of Doxorubicin-Containing Low Temperature Sensitive Liposomes in Spontaneous Canine Tumors," *Clin Cancer Res*; 12(13); pp. 4004-4010 (2006).

Nallamothu, Ramakrishna, et al., "A Tumor Vasculature Targeted Liposome Delivery System for Combretastatin A4: Design, Characterization, and In Vitro Evaluation," *AAPS PharmSciTech*, 7(2) Article 32, (2006).

Zhang, Yin, et al., "Multimodality Imaging of Integrin $\alpha_v \beta_3$ Expression," *Theranostics*, 1, pp. 135-148 (2011).

* cited by examiner the disclosure of Korean Patent Application No. 10-2012-0010506 is incorporated herein in its entirety by reference.

LIPOSOME COMPRISING ELASTIN-LIKE POLYPEPTIDE AND TUMOR CELL TARGETING MATERIAL AND USE THEREOF

CROSS-REFERENCE TO RELATED APPLICATIONS

This application claims the benefit of Korean Patent Application No. 10-2012-0010506, filed on Feb. 1, 2012, and Korean Patent Application No. 10-2011-0107055, filed on Oct. 19, 2011; the disclosure of Korean Patent Application No. 10-2012-0010506 is incorporated herein in its entirety by reference.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 12,565 Byte ASCII (Text) file named PX40487US_SEQ_amendment_170515" created on May 15, 2017.

BACKGROUND

The present disclosure relates to a liposome including an elastin-like polypeptide (ELP) and a tumor cell targeting material, a pharmaceutical composition including the liposome, and a method of delivering an active agent to a target site using the liposome.

Liposomes consist of at least one lipid bilayer membrane enclosing an aqueous internal compartment. Liposomes may be characterized by membrane type and by size. Small unilamellar vesicles (SUVs) have a single membrane and typically range between 20 and 50 nm in diameter. Large unilamellar vesicles (LUVs) are typically larger than 50 nm. Oligolamellar large vesicles and multilamellar vesicles have multiple, usually concentric, membrane layers and are typically larger than 100 nm. Liposomes with several nonconcentric membranes, i.e., several smaller vesicles contained within a larger vesicle, are termed multivesicular vesicles.

Liposomes are formulated to carry drugs or other active agent either contained within the aqueous interior space (water-soluble active agent) or partitioned into the lipid bilayer (water-insoluble active agent).

Active agents which have short half-lives in the bloodstream are particularly suited to delivery via liposomes. Many anti-neoplastic agents, for example, are known to have a short half-life in the bloodstream and thus, their parenteral use is not feasible. However, the use of liposomes for site-specific delivery of active agent via the bloodstream is severely limited by the rapid clearance of liposomes from the blood by cells of the reticuloendothelial system (RES).

Liposomes are not normally leaky unless a hole is formed in the liposome membrane, unless the membrane degrades or dissolves, or unless a temperature of the membrane increases to a phase transition temperature. The elevation of temperature at a target site in a subject (hyperthermia) may increase the temperature of the liposome to a phase transition temperature or higher and thus liposome contents may be released. This procedure may be used for the selective delivery of a therapeutic agent. However, this technique is limited where the phase transition temperature of the liposome is significantly higher than the normal tissue temperature.

It is accordingly desirable to devise liposome formulations capable of efficiently delivering an active agent.

SUMMARY

Provided is a liposome including an elastin-like polypeptide (ELP) and a tumor cell targeting material.

Provided is a pharmaceutical composition including the liposome including an ELP and a tumor cell targeting material containing an active agent.

Provided is a method of efficiently delivering an active agent to a target site in the body of an individual by using the liposome.

Additional aspects will be set forth in part in the description which follows and, in part, will be apparent from the description, or may be learned by practice of the presented embodiments.

BRIEF DESCRIPTION OF THE DRAWINGS

These and/or other aspects will become apparent and more readily appreciated from the following description of the embodiments, taken in conjunction with the accompanying drawings of which.

DETAILED DESCRIPTION

Figure 1:
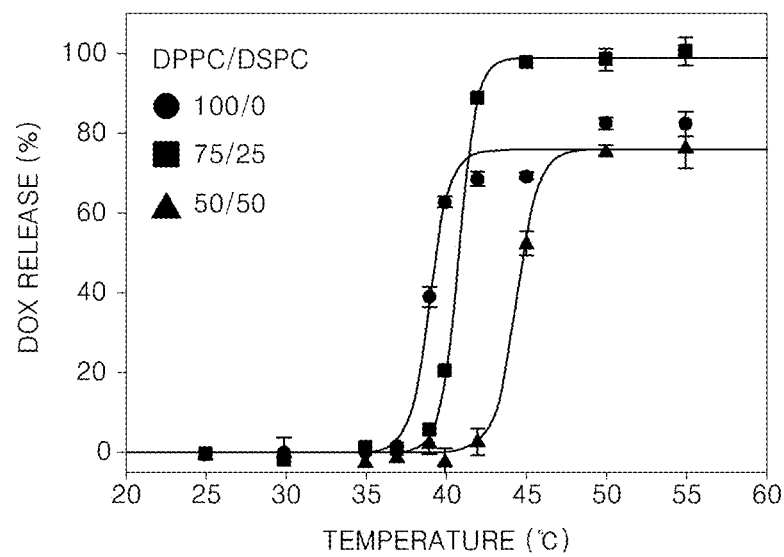
FIG. 1 is a graph showing temperature release profiles of doxorubicin (DOX) from liposomes prepared in Examples 1 to 3 using SA-V3-NH$_2$ that is stearoyl-VPGVG VPGVG VPGVG-NH$_2$ (SEQ ID NO: 7), DSPC+DPPC, DSPE-PEG, and cholesterol with a molar ratio of 0.55:55:2:10, where molar ratios of DPPC/DSPC used were 100/0 (Example 1), 75/25 (Example 2), and 50/50 (Example 3)

According to an embodiment of the present invention, a liposome includes a lipid bilayer; elastin-like polypeptide (ELP) conjugated to one or more hydrophobic moieties; and a lipid bilayer stabilizing agent, wherein the hydrophobic moieties are packed in the lipid bilayer, and the lipid bilayer includes one or more lipids to which a tumor cell targeting material is bound.

The term "tumor cell targeting material" is a material that may be more prominently delivered to a tumor cell or around tumor cells than to other regions of a host (e.g., animal, mammal or human) upon administration. The material may be a material that is specifically bound to a tumor cell, specifically taken up by a tumor cell, or specifically bound to a vessel around a tumor, which is a tumor vasculature. The term "a material specifically bound to a tumor vasculature" includes a material that binds to another material that exists in greater abundance in a tumor vasculature than in a normal vasculature. A tumor vasculature may be morphologically and functionally different from that found in most normal (non-cancerous or non-tumorous) adult tissues. Common features of vessels including a tumor microcirculation, which is a tumor vasculature, are dilated and elongated shapes, blind ends, bulges and leaky sprouts, abrupt changes in diameter, extensive tortuosity, and evidence of vascular compression. The material may be a material that is specifically present in a tumor vasculature cell or an environment other than the tumor vasculature cell, for example, a receptor-binding ligand or an antibody.

The tumor cell targeting material may be, for example, a peptide including a RGD sequence or its derivative, biotin or its derivative, folate or its derivative, an antibody specific to an antigen of a tumor cell, an antibody fragment or its derivative specific to an antigen of a tumor cell, a ligand or its derivative, or a combination thereof. The material may be a peptide including a RGD sequence (e.g., a cyclic peptide including a RGD sequence) or its derivative. The cyclic peptide including a RGD sequence may include cyclic tetrapeptide, cyclic pentapeptide, cyclic hexapeptide, cyclic heptapeptide, or cyclic octapeptide. The material may be a cyclic R*GDYK* (SEQ ID NO:11) peptide, * indicating a location of a cyclized amide bond (—CO—NH—). The material, as a cyclic peptide including the RGD sequence, may have a RGD sequence, a cyclized amide bond (—CO—NH—), and an active hydrosulfide group at a terminal of a cysteine. An amino acid sequence of the cyclic peptide is X*YRGDY'Z* (SEQ ID NO:12), where * indicates a location of the cyclization, X represents a cysteine residue including a free hydrosulfide group, Y and Y' represent one or more amino acids, or an amino acid sequence of an appropriate length, respectively, and Z represents an amino acid that may form a ring together with a cysteine residue. An amino acid sequence of the cyclic peptide may be X*GRGDSPZ* (SEQ ID NO:13), where * indicates a location of the cyclization, X represents a cysteine residue including a free hydrosulfide group, and Z represents one or more amino acids, or an amino acid sequence of an appropriate length. An amino acid sequence of the cyclic peptide may be X*GRGDSPK* (SEQ ID NO:14), where * indicates a location of the cyclization and X represents a cysteine residue including a free hydrosulfide group. The peptide including the RGD sequence or its derivative may be bound to a lipid by an appropriate linker such as a succinyl group. Examples of RGD containing cyclic peptides include cyclo(Arg-Gly-Asp-D-Phe-Cys)* (SEQ ID NO:15) (c(RGDfC, M.W. 578.65, linker additions via Cys)

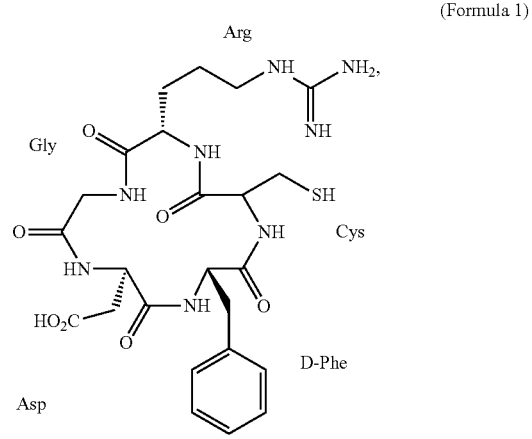 [SMILES: N=C(N)NCCC[C@@H]1NC(=O)C(CS)NC(=O)[C@H](Cc2ccccc2)NC(=O)[C@@H](CC(=O)O)NC(=O)CNC1=O]

(Formula 1)

cyclo(Arg-Gly-Asp-D-Phe-Lys)* (SEQ ID NO:16) (c(RGDfK), M.W. 603.68, $\alpha_v\beta_3$ integrin binding RGD peptide)

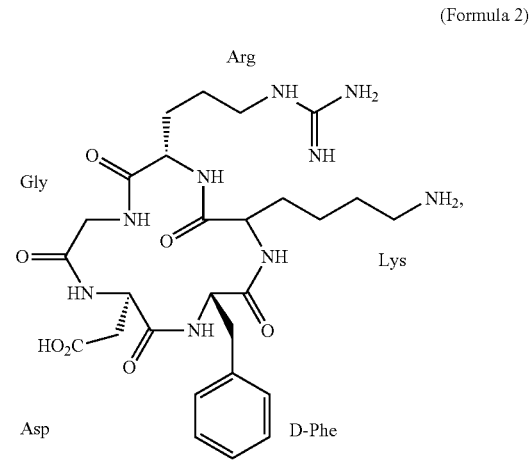 [SMILES: N=C(N)NCCC[C@@H]1NC(=O)C(CCCCN)NC(=O)[C@H](Cc2ccccc2)NC(=O)[C@@H](CC(=O)O)NC(=O)CNC1=O]

(Formula 2)

cyclo [Arg-Gly-Asp-D-Phe-Lys(PEG-PEG)]* (SEQ ID NO:17) (c(RGDfK(PEG-PEG), where PEG=8-amino-3,6-dioxaoctanoic acid, RGD peptide equipped with PEG spacers for more efficient binding to lipid surfaces)

(Formula 3)

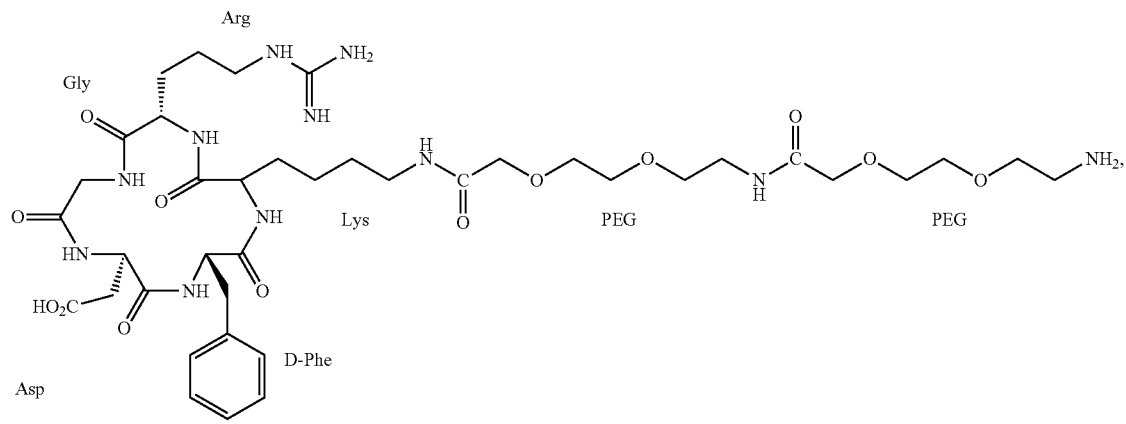

and cyclo [Arg-Gly-Asp-D-Phe-Lys (Ac-SCH2CO) (SEQ ID NO:18)]& (c[RGDfK(Ac-SCH2CO)], RGD peptide equipped with thioacetyl group for linking to liposome)

(Formula 4)

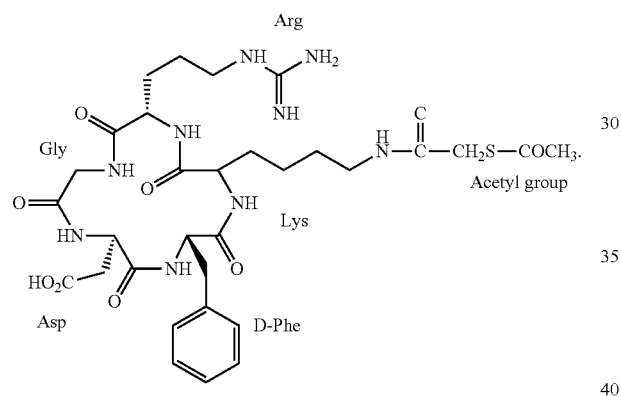

The first lipid may be a DSPE-cRGDYK (SEQ ID NO:19) molecule having Formula 5 below. Here, a peptide including the RGD sequence or its derivative may be a cRGDYK-$R_1$- (SEQ ID NO:27), wherein $R_1$ is —C(O)—($R_2$)—C(O)— wherein $R_2$ is $C_1$-$C_{50}$ alkylene. $R_1$ may be —C(O)—$(CH_2)_n$—C(O)— moiety, wherein n is 1 to 50. The DSPE-cRGDYK (SEQ ID NO:19) molecule includes salts thereof, stereoisomer thereof, or a combination thereof. The salts may be salts including H+, Li, Na+, K+, Rb+, Cs+, or Fr+.

(Formula 5)

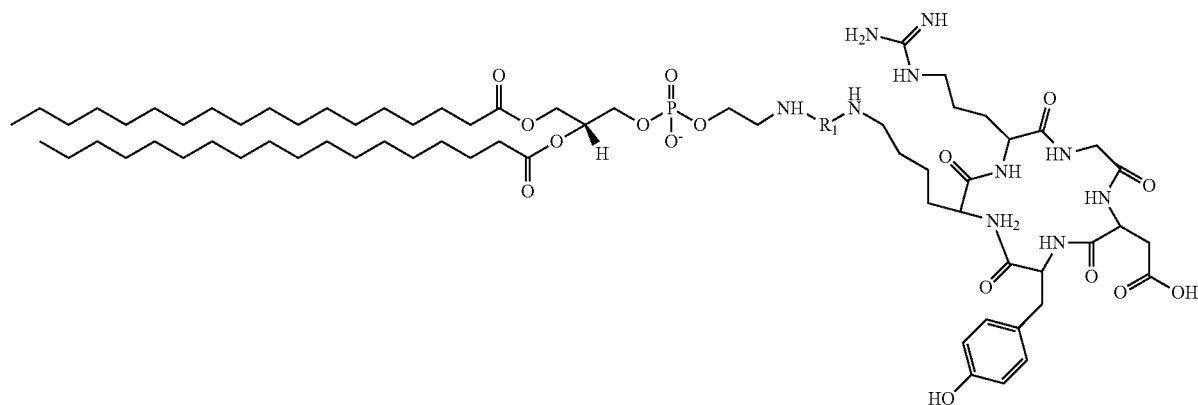

The first lipid may be a DSPE-cRGDYK(SEQ ID NO:19) molecule or any phospholipid that is connected with a cRGDYK (SEQ ID NO:20) moiety itself or connected with a cRGDYK (SEQ ID NO:20) moiety through a linker such as —C(O)—(CH$_2$)$_3$—C(O)—, for instance, a molecule of Formula 4, wherein R1 is —C(O)—(CH$_2$)$_3$—C(O)—. The linker may include a polyethylene glycol (PEG) moiety. The phospholipid may be one or more C12 to C24 fatty acid esters. The first lipid may be a DSPE-PEG-cRGDyK (SEQ ID NO:21) molecule, which includes PEG moiety in the linker region. The term "PEG moiety" refers to a moiety including —[OCH$_2$CH$_2$]—. The PEG moiety may include 1-1,000, for example, 1-700, 1-500, 1-400, 1-300, 1-200, 1-100, 1-50, 1-30, 1-20, 1-10, 1-8, 1-6, 1-5, 1-4, 1-3, 2-500, 2-400, 2-300, 2-200, 2-100, 2-50, 2-30, 2-20, 2-10, 2-8, 2-6, 2-5, 2-4, 2-3, 3-500, 3-400, 3-300, 3-200, 3-100, 3-50, 3-30, 3-20, 3-10, 3-8, 3-6, 3-5, or 3-4 of —[OCH$_2$CH$_2$]—. For example, the DSPE-PEG-cRGDyK (SEQ ID NO:21) molecule may have Formula 5, wherein R$_1$ is —C(O)—(R$_2$)— C(O)— wherein R$_2$ may be a PEG moiety. R$_2$ may be —[OCH$_2$CH$_2$]$_n$—O(CH$_2$)$_p$—NH—C(O)—(CH$_2$)$_q$— moiety, wherein n, p, and q is an integer of 1 to 250, respectively. For example, n p and q are each, independently, an integer of 1 to 200, 1 to 150, 1 to 100, 1 to 75, 1 to 50, 2 to 250, 2 to 200, 2 to 150, 2 to 100, 2 to 75, or 2 to 50. Further, n may be an integer of 2 to 50, and p and q may each, independently, be 1-10, for example, 1, 2, 3, 4, 5, 6, 7, 8, 9, or 10, respectively. An example of R$_1$ is —C(O)—[OCH$_2$CH$_2$]$_n$—O(CH$_2$)$_3$—NH—CO—(CH$_2$)$_3$—C(O)—. The DSPE-PEG_cRGDYK (SEQ ID NO:21) molecule includes salts thereof, stereoisomer thereof, or a combination thereof. The salts may be salts including H+, Li, Na+, K+, Rb+, Cs+, or Fr+.

The material is a separated peptide including an amino acid sequence selected from CRGRRST (SEQ ID NO: 8), CRSRKG (SEQ ID NO: 9), and CKAAKNK (SEQ ID NO: 10) having a length of 60 amino acid residues or less, and the peptide may selectively home to a premalignant pancreatic vasculature, a malignant pancreatic vasculature, or a pancreatic tumor cell.

The term "lipid bilayer" as used herein indicates a membrane composed of two layers of lipid. The lipid layer may have a similar thickness as that of a naturally existing bilayer, for example, a cell membrane, a nuclear membrane, or a virus envelope. Examples of the thickness of the lipid bilayer may be 10 nm or less, for example, about 1 nm to about 9 nm, about 2 nm to about 8 nm, about 2 nm to about 6 nm, about 2 nm to about 4 nm, or about 2.5 nm to about 3.5 nm. The lipid bilayer is the barrier that keeps ions, proteins, and other molecules where they are needed and prevents them from diffusing into areas where they should not be. Natural bilayers are usually made mostly of phospholipids. A phospholipid has a hydrophilic head and two hydrophobic tails. When phospholipids are exposed to water, they arrange themselves into a two-layered sheet (a bilayer) with all of their tails pointing toward the center of the sheet. The center of this bilayer contains almost no water and also excludes molecules like sugars or salts that dissolve in water but not in oil. Phospholipids with certain head groups can alter the surface chemistry of a bilayer. Also, lipid tails may affect membrane properties, for instance by determining the phase of the bilayer. The bilayer can adopt a solid gel phase state at lower temperatures but undergo phase transition to a fluid state at higher temperatures. The packing of lipids within the bilayer also affects its mechanical properties, including its resistance to stretching and bending. Biological membranes typically include several types of lipids other than phospholipids. A particularly important example in animal cells is cholesterol, which helps strengthen the bilayer and decrease its permeability.

A "lipid" for constructing the lipid bilayer may be a molecule having a hydrophilic head and hydrophobic tails. The lipid may have 12 to 50 carbon atoms. The lipid may be phospholipid. The phospholipid may have 16 to 24 carbon atoms. The phospholipid may be at least one selected from the group consisting of phosphatidyl choline, phosphatidyl glycerol, phosphatidyl inositol, phosphatidyl ethanolamine and a combination thereof, wherein the at least one phospholipid have two acyl groups. Also, the phospholipid may have a phase transition temperature of about 10° C. to about 70° C., for example, about 38 to about 45° C. The acyl group of the phospholipid may be saturated or unsaturated. The phospholipid may be a mixture of two or more phospholipids. A lipid bilayer having various phase transition temperatures may be produced due to the mixture of two or more phospholipids.

A phospholipid may have two acyl groups, for example, one selected from the group consisting of C12 saturated chain phospholipid (Tc=about 10° C.), a C14 saturated chain phospholipid (Tc=about 24° C.), a C16 saturated chain phospholipid (Tc=about 41° C.), a C18 saturated chain phospholipid (Tc=about 55° C.), a C20 saturated chain phospholipid (Tc=about 65° C.), a C22 saturated chain phospholipid (Tc=about 70° C.), and a combination thereof. Similarly, other common phospholipids that may be used include phosphatidyl glycerols, phosphatidyl inositols, phosphatidyl ethanolamines, sphingomyelins and gangliosides that, as with the phosphatidylcholines, have phase transition temperatures that vary in a similar fashion dependent on their acyl chain length.

An example of the C16 saturated chain phospholipid may be dipalmitoylphosphatidylcholine (DPPC). DPPC is a saturated chain (C16) phospholipid with a bilayer transition temperature of about 41.5° C. An example of the C18 saturated chain phospholipid may be 1,2-distearoyl-sn-glycero-3-phosphocholine (DSPC). DSPC is a saturated chain (C18) phospholipid with a bilayer transition temperature of about 55.10° C.

Other membrane-forming materials may be used which are not phospholipids. Exemplary materials which may form a solid-phase membrane include bola lipids or bacterial lipids. Additionally, block copolymers including a water-soluble polymer (e.g., polyethylene glycol) and a water-insoluble polymer (e.g., polypropylene oxide and polyethylethylene) may be employed.

As used herein, the "primary lipid" in a liposome bilayer is the main lipid component of liposome bilayer material. Thus, for example, in a liposome bilayer composed of 70 mole % phospholipid and 30 mole % cholesterol, the phospholipid is the primary lipid.

A lipid bilayer may have different phase behaviors with temperature. At a given temperature, a lipid bilayer may exist in either a liquid or a gel (solid) phase. All lipids have a characteristic temperature at which they transition from the gel to liquid phase. In both phases, the lipid is prevented from flip-flopping across the bilayer, but in liquid phase, bilayer a given lipid will exchange locations with its neighbor. This random walk exchange allows lipids to diffuse and thus wander across the surface of the membrane. Unlike liquid phase bilayer, the lipids in a gel phase bilayer are locked in place.

The phase behavior of a lipid bilayer is largely determined by the strength of the attractive forces of Van der Waals interactions between adjacent lipids. Longer tailed lipids have more area over which to interact, increasing the strength of this interaction and consequently decreasing the lipid mobility. Thus, at a given temperature, a short-tailed lipid will be more fluid than an otherwise identical long-tailed lipid. Transition temperature may also be affected by the degree of unsaturation of the lipid tails. An unsaturated double bond may produce a kink in the alkane chain, disrupting the lipid packing. This disruption creates extra free space within the bilayer which allows additional flexibility in the adjacent chains.

Most natural membranes are a complex mixture of different lipids. If some of the components are liquid at a given temperature while others are in the gel phase, the two phases can coexist in spatially separated regions, rather like an iceberg floating in the ocean.

As used herein, the term "phase transition temperature" indicates the temperature at which a material changes from a solid phase to a liquid phase (also called a melting temperature) or from a liquid phase to a solid phase. The material includes lipid, a lipid bilayer or a liposome not including ELP conjugated to hydrophobic moieties, or a lipid bilayer or a liposome including ELP conjugated to hydrophobic moieties.

The liposome includes ELP conjugated to hydrophobic moieties, wherein the hydrophobic moieties are packed in the lipid bilayer.

Each of the hydrophobic moieties composes a lipid bilayer by being packed in the lipid bilayer. The hydrophobic moiety may be molecules having a property of immobilizing the ELP conjugated thereto to the lipid bilayer, for example, hydrophobic property. The hydrophobic moieties may be entirely or partially packed in the lipid bilayer. The hydrophobic moieties may be the same lipids composing the lipid bilayer or other lipids.

The hydrophobic moiety may include molecules only containing a hydrophobic region or amphipathic molecules containing both hydrophilic and hydrophobic regions. In the amphipathic molecules containing both hydrophilic and hydrophobic regions, the hydrophobic region may be arranged inwardly of the lipid bilayer, and the hydrophilic region may be arranged outwardly of the lipid bilayer and linked with ELP. Here, "outwardly" indicates a direction away from a center of the lipid bilayer, that is, inward of the liposome or outward of the liposome.

The hydrophobic moiety may be a lipid naturally existing in a biomembrane or a lipid that a lipid bilayer may be comprised of, even though not naturally existing in a biomembrane.

The lipid naturally existing in a biomembrane may be one selected from phospholipid or its derivative, sterol or its derivative, sphingolipid or its derivative, and a combination thereof. The phospholipid or its derivative may be one selected from the group consisting of phosphatidyl choline, phosphatidyl glycerol, phosphatidyl inositol, phosphatidyl ethanolamine, and a combination thereof. The sterol or its derivative may be cholesterol or its derivative, or squalene or its derivative. The sphingolipid may be sphingomyelin or its derivative, or ganglioside or its derivative. The phospholipid, sterol, or sphingolipid includes an intermediate or a precursor produced during a synthesis process in vivo. For example, the hydrophobic moiety includes phosphoglyceride, sphingosine, ceramide, or cerebroside.

The hydrophobic moiety may be a saturated or unsaturated hydrocarbon group, a saturated or unsaturated acyl-group, or a saturated or unsaturated alkoxygroup.

A conjugation of a hydrophobic moiety and an ELP may be effected by way of a non-cleavable linkage (e.g., a linkage that is not cleaved under physiological and pathological conditions) or by a cleavable linkage (a linkage that is cleaved upon administration under physiological or pathological conditions). An example of the cleavable linkage may be a linkage mediated by a pH cleavable linker, a heat cleavable linker, a radiation cleavable linker, or a linker that is cleaved in aqueous solution.

The hydrophobic moiety may be conjugated or bound to the ELP by a nitrogen atom at a N-terminus of the ELP, or a carbonyl (—C(O)—) group at a C-terminus of the ELP. Also, the hydrophobic moiety may be conjugated by an interaction with a functional group on a side chain of the ELP, such as an amino group, a carbonyl group, a hydroxyl group, a thiol group, or combination thereof. The hydrophobic moiety may be conjugated to the ELP by an amine bond or amide bond with the nitrogen atom of the ELP. The hydrophobic moiety may be conjugated to the ELP by an amide or ester bond with the carbonyl group at the C-terminus of the ELP. Furthermore, if the hydrophobic moiety is branched, or has more than one hydrophobic chain, the hydrophobic moiety can be conjugated to the ELP at any branch or chain of the hydrophobic moiety.

The hydrophobic region of the hydrophobic moiety may have 4 to 30 carbon atoms, for example, 14 to 24 carbon atoms or 16 to 24 carbon atoms. The hydrophobic moiety may be, for example, myristoyl (C14), palmitoyl (C16), stearoyl (C18), arachidonyl (C20), behenoyl (C22), or lignoceroyl (C24). The hydrophobic moiety may be packed in a lipid bilayer by a hydrophobic effect, and accordingly, the ELP conjugated to the hydrophobic moiety may be immobilized on the liposome.

As used herein the term "elastin-like polypeptides" refers to a class of amino acid polymers that undergo a conformation change dependent upon temperature. In an embodiment of the present invention, the ELP may be polymers exhibiting inverse phase transitioning behavior. Inverse phase transitioning behavior indicates that the ELP is soluble in aqueous solutions below an inverse transition temperature ($T_t$), but the ELP is insoluble as the temperature is raised higher than $T_t$. By increasing the temperature ELP transition from elongated chains that are highly soluble into tightly folded aggregates with greatly reduced solubility. Such inverse phase transition may be induced by ELP structures having more β-turn structures and distorted β-structures as temperature increases. The ELP may have a phase transitioning temperature within a range from about 10 to about 70° C.

When ELP is linked to the compartments of a lipid bilayer, the inverse phase transitioning behavior may destroy the lipid bilayer due to shrinkage and self-assembly of the ELP as temperature rises from a temperature lower than $T_t$ of ELP to a higher temperature. Destroying the lipid bilayer may increase the permeability of the lipid bilayer. Thus, active agent contained in a liposome including the lipid bilayer may be released with a higher permeability from the liposome. However, one or more embodiments of the present invention are not limited to any particular mechanism.

The destruction of the lipid bilayer in a liposome due to the inverse phase transitioning behavior of ELP may differ according to lipids of the lipid bilayer, or the phase transition temperature of the lipid bilayer. A lipid bilayer may exist in a gel phase at the phase transition temperature or below and in a liquid (crystalline) phase at the phase transition temperature or above. When the lipid bilayer exists in a gel phase, destruction of the lipid bilayer may not occur or may be limited, though a structure of ELP changes to have a β-turn structure due to the inverse phase transitioning behavior. On the other hand, when the lipid bilayer exists in a liquid phase, the destruction of the lipid bilayer may be induced as a structure of ELP changes to have a β-turn structure due to the inverse phase transitioning behavior. In other words, when the lipid bilayer exists in a liquid phase rather than in a gel phase, the inverse phase transition induces destruction of the lipid bilayer more efficiently. Therefore, a releasing temperature of active agent contained in a liposome may be controlled by adjusting the phase transition temperature of a lipid bilayer of the liposome or the inverse phase transition temperature of ELP. For example, the phase transition temperature of a lipid bilayer or a liposome including ELP may be within a range from about 10 to about 70° C., for example, about 39 to about 45° C.

A liposome including an ELP according to one or more embodiments may be used for efficiently releasing active agent contained in the liposome compared to a liposome not including an ELP but only a lipid bilayer. When simply a phase transition of lipids of a lipid bilayer is used, the release of active agent in a liposome is induced by dispersion of the lipids. Meanwhile, when a liposome including an ELP is used, a further release of active agent may be induced by the inverse phase transition behavior of ELP, in other words, further release of active agent may be induced by a destroyed lipid bilayer due to shrinkage and assembly of ELPs. Here, the active agent may be contained in an interior space of the liposome, in an interior of the lipid bilayer, or in both. Also, due to interaction between the material and a tumor or around a tumor, such as a tumor vasculature, the liposome may be conveniently delivered to a tumor or a tumor vasculature or time the liposome staying in a tumor vasculature may be increased.

The liposome includes a stabilizing agent. In the case of liposomes including an ELP, when a lipid bilayer stabilizing agent employed to increase stability of a lipid bilayer are present in the lipid bilayer, the active agent may be efficiently released. The stabilizing agent may be lipids which have a phase transition temperature of the lipid bilayer or higher, preferably higher. The lipid bilayer stabilizing agent may be one selected from the group consisting of steroid or its derivative, sphingolipid or its derivative, and a combination thereof. The lipid bilayer stabilizing agent may be steroid with a property enabling incorporation into a lipid bilayer. As used herein, the term "steroid" indicates a type of organic compound including a core of gonane or a skeleton derived therefrom that contains a specific arrangement of four cycloalkane rings that are joined to each other, in other words, three cyclohexane rings designated as rings A, B, and C from left to right, and one cyclopentane ring (the D ring). Here, "a skeleton derived therefrom" includes an unsaturated bond in the gonane skeleton. The steroid may vary in terms of the functional groups attached to the four ring core and the oxidation state of the rings. For example, the steroid may include a hydrophilic functional group on the ring. For example, the steroid may have a hydroxyl group. The steroid may be sterol. The term "sterol" is a type of steroid which has the hydroxyl group at position C-3 and has a skeleton derived from cholestane. Here, the term "derived skeleton" includes an unsaturated bond introduced in the cholestane skeleton. The steroid includes steroid found in plants, animals, and fungi. For example, all steroid may be made in cells either from lanosterol as in animals and fungi, or from cycloartenol as in plants. The sterol includes cholesterol or its derivative. Here, "derivative" means a derivate of cholesterol which maintains a property to be inserted in a lipid bilayer. The derivative includes a fatty acid ester of cholesterol. The fatty acid may be a C6 to C50 fatty acid. The stabilizing agent may be one selected from the group consisting of cholesterol, sitosterol, ergosterol, stigmasterol, 4,22-stigmastadien-3-one, stigmasterol acetate, lanosterol, cycloartenol, and a combination thereof.

When a liposome including a simple lipid bilayer not including an ELP contains the stabilizing agent, for example cholesterol, the release of active agent may be significantly reduced. Thus, in the case of a liposome including an ELP, by using a lipid bilayer stabilizing agent, the active agent may be efficiently released while maintaining stability of a lipid bilayer or of the liposome. In particular, in a narrow range of temperature, for example in a range of about 39° C. to about 45° C., drugs may be efficiently released.

An ELP may be defined by its amino acid sequence. For example, a part of, or an entire, ELP may include one or more repeating units which may be one selected from VPGXG (SEQ ID NO: 1), PGXGV (SEQ ID NO: 2), GXGVP (SEQ ID NO: 3), XGVPG (SEQ ID NO: 4), GVPGX (SEQ ID NO: 5) and a combination thereof, where V is valine, P is proline, G is glycine, and X is any natural or non-natural amino acid except proline. Here, X in each repeating unit may be the same or different amino acid. The repeating units may be separated by one or more amino acids that do not remove a phase transition property of an obtained ELP, or an end portion may become the one or more amino acids or other linker moieties. A weight ratio of the repeating units verses the other amino acids or linker moieties may be about 0.1 to about 99.9%, for example, about 1 to about 99.9%, about 10 to about 99.9%, about 20 to about 99.9%, about 30 to about 99.9%, about 40 to about 99.9%, about 50 to about 99.9%, about 60 to about 99.9%, about 70 to about 99.9%, about 80 to about 99.9%, about 90 to about 99.9%, or about 95.0 to about 99.9% of the repeating units out of both the repeating units and the other amino acids. The selected repeating unit may be repeated twice or more, for example, 2 to 200 times, for example, 2 to 100, 2 to 80, 2 to 60, 2 to 40, 2 to 10, 2 to 12, 2 to 8, 2 to 6, 4 to 100, 8 to 80, 10 to 60, 12 to 40, 20 to 40, 4 to 10, 4 to 8, or 4 to 6 times.

In an embodiment of the present invention, the ELP may be blocks where VPGXG (SEQ ID NO: 1), PGXGV (SEQ ID NO: 2), GXGVP (SEQ ID NO: 3), XGVPG (SEQ ID NO: 4), GVPGX (SEQ ID NO: 5) or a combination thereof is tandemly repeated, or the ELP may include blocks where VPGXG (SEQ ID NO: 1), PGXGV (SEQ ID NO: 2), GXGVP (SEQ ID NO: 3), XGVPG (SEQ ID NO: 4), GVPGX (SEQ ID NO: 5) or combinations thereof is tandemly repeated. As long as the inverse phase transition behavior is maintained, the ELP may be composed of VPGXG (SEQ ID NO: 1), PGXGV (SEQ ID NO: 2), GXGVP (SEQ ID NO: 3), XGVPG (SEQ ID NO: 4), GVPGX (SEQ ID NO: 5) or combinations thereof and may include another portion in a molecule, for example a linker and blocking group. An N-terminus or C-terminus of the ELP may be linked with a hydrophobic moiety. Also, a hydrophobic moiety may be conjugated to an ELP by linking with a reactive group among a side chain of amino acid residue in the ELP. The reactive group may be an amino group, a hydroxyl group, a thiol group, or a carboxyl group. The other terminus not linked with a hydrophobic moiety may be blocked or unblocked. For example, when a hydrophobic moiety and an ELP are linked via the N-terminus of the ELP, a carboxyl group of the C-terminus of ELP may be blocked or unblocked. The blocking may be enabled by linking or interacting with a material that may be biocompatible, non-immunogenic, helpful in a specific delivery, or escapable from biological degradation system. For example, the blocking may be enabled by an amide bond formed by binding a carboxyl group of a C-terminus of ELP and an amino group. The amino group may be an ammonia molecule (i.e., forming —CO—NH$_2$), a primary amine, a secondary amine, or a tertiary amine. The primary, secondary, or tertiary amine may each have 1 to 10 carbon atoms, for example, 1 to 6 carbon atoms. X may be valine or alanine.

The repeating units may be each independently included in an ELP with one or more integer number of repetition. The number of repetitions may be each independently an integer of 2 to 200, 2 to 100, 2 to 80, 2 to 60, 2 to 40, 2 to 10, 2 to 12, 2 to 8, 2 to 6, 4 to 100, 8 to 80, 10 to 60, 12 to 40, 20 to 40, 4 to 10, 4 to 8, or 4 to 6.

In the liposome, a molar ratio of primary lipids of the lipid bilayer:an ELP conjugated to a hydrophobic moiety may be appropriately selected according to a property of the selected lipid bilayer and a property of the ELP conjugated to a hydrophobic moiety. For example, a molar ratio of primary lipids:an ELP conjugated to a hydrophobic moiety may be about 50 to about 99.9:about 0.1 to about 50. For example, a molar ratio of primary lipids (DPPC or mixtures of DPPC and DSPC): an ELP conjugated to a hydrophobic moiety Liposomes may not accumulate in leaky tumor tissue because of their relatively short half life in blood circulation due to their rapid uptake by macrophages of the liver and spleen (organs of the endothelial system or reticuloendothelial system (RES)). Liposome preparation may be devised to escape from rapid RES uptake and thus increase circulation times. The lipid bilayer may contain, for example, a lipid derivative derivatized with a hydrophilic polymer, for example a phospholipid derivative. The hydrophilic polymer may be selected from polyethylene glycol (PEG), polylactic acid, polyglycolic acid, copolymer of polylactic acid and polyglycolic acid, polyvinyl alcohol, polyvinyl pyrrolidone, oligosaccharide, and a mixture thereof. The derivative may be a phospholipid of C4-C30, for example C16-C24, conjugated with PEG. The derivative may be DPPC-PEG or DSPE-PEG. The PEG may have a molecular weight of about 180 to about 50,000 Da. The DSPE-PEG may have a structure of Formula 6 where X is H, or protecting group, such as C1-C20 alkoxy group, including a methoxy group, a ethoxy group, or a propoxy group. In Formula 3, a molecular weight of the PEG may be about 2000 Da, about 5000 Da, about 10000 Da, or about 20000 Da.

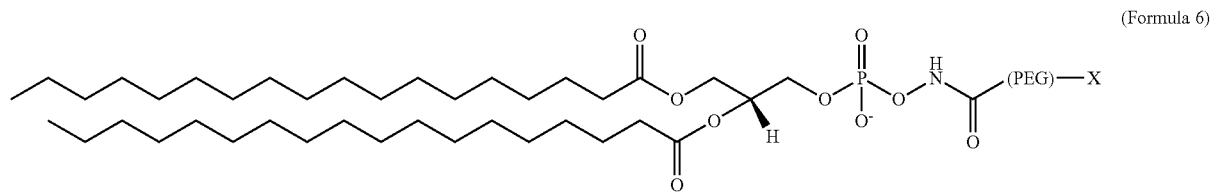

(Formula 6)

(palmitoyl-(VPGXG)n-NH$_2$ (SEQ ID NO:22) or stearoyl-(VPGXG)n-NH$_2$ (SEQ ID NO:23), where n is 2 to 12) may be about 50 to about 99.0:about 0.1 to about 50. Stearoyl-(VPGXG)n-NH$_2$ (SEQ ID NO:23), where n is 6 is set forth in SEQ ID NO: 6.

In the liposome, the lipid bilayer may include a lipid bilayer stabilizing agent in the midst of the lipid bilayer to increase stability of the lipid bilayer. The stabilizing agent may be lipids having a higher phase transition temperature than a phase transition temperature of the lipid bilayer. The stabilizing agent may be sterol or glycolipid. The sterol may be cholesterol or its derivative. The stabilizing agent, for example cholesterol, may help to strengthen the lipid bilayer and reduce its permeability. Therefore, the stabilizing agent, for example cholesterol, enables liposomes to exist stably at normal body temperature. A molar ratio of primary lipid:the stabilizing agent, for example cholesterol, may be about 50 to about 99.9:about 0.1 to about 50. The ratio of the primary lipid:the stabilizing agent may be about 50 to about 99.9: about 0.1 to about 50, for example about 50 to about 99.9:about 3 to about 50, about 50 to about 99.9:about 5 to about 50, about 50 to about 99.9:about 7 to about 50, about 50 to about 99.9:about 9 to about 50, about 50 to about 99.9:about 11 to about 50, about 50 to about 99.9:about 15 to about 50, about 50 to about 99.9:about 20 to about 50, about 50 to about 99.9:about 20 to about 35, about 50 to about 99.9:about 20 to about 30, about 50 to about 99.9: about 25 to about 30, about 50 to about 99.9:about 25 to about 50, about 50 to about 99.9:about 30 to about 50, about 50 to about 99.9:about 35 to about 50, about 50 to about 99.9:about 1 to about 35, about 50 to about 99.9:about 3 to about 30, about 50 to about 99.9:about 5 to about 25, about 50 to about 99.9:about 7 to about 20, or about 50 to about 99.9:about 9 to about 15.

The liposomes may be unilamellar vesicles (SUV) or multivesiclular vesicles. A diameter of the liposomes may be about 50 nm to about 500 nm, for example, about 50 nm to about 400 nm, about 50 nm to about 300 nm, about 50 nm to about 200 nm, about 100 nm to about 500 nm, about 100 nm to about 400 nm, about 100 nm to about 300 nm, or about 100 nm to about 200 nm.

In an embodiment of the present invention, the lipid bilayer may include a phospholipid, an ELP conjugated to a hydrophobic moiety, a phospholipid derivative derivatized with a hydrophilic polymer, and cholesterol. The phospholipid, an ELP conjugated to a hydrophobic moiety, a phospholipid derivative derivatized with a hydrophilic polymer, and cholesterol in the lipid bilayer is as mentioned above.

In the embodiment, the phospholipid:an ELP with a hydrophobic moiety:a phospholipid derivative derived with a hydrophilic polymer:and cholesterol may have a molar ratio of about 50 to about 99.9:about 0.1 to about 50:about 0 to about 10:about 0.1 to about 50, for example, about 50 to about 99.9:about 0.1 to about 50:about 0 to about 10:about 20 to about 50, about 50 to about 99.9:about 0.1 to about 50:about 0 to about 10:about 20 to about 30, about 50 to about 99.9:about 0.1 to about 50:0 to about 10:about 25 to about 30, about 50 to about 99.9:about 0.1 to about 50:about 0 to about 10:about 20 to about 50, about 50 to about 99.9:about 0.1 to about 50:about 0 to about 10:about 20 to about 30, or about 50 to about 99.9:about 0.1 to about 50:about 0 to about 10:about 25 to about 30.

The phospholipid may be DPPC. The phospholipid may be a mixture of DPPC and DSPC. The phospholipid may have a molar ratio of DPPC:DSPC that is about 1:about 0 to about 0.5, for example, about 1:about 0.1 to about 0.5. The ELP conjugated to a hydrophobic moiety may include: the hydrophobic moiety having a acyl group, the ELP including (VPGXG)n (SEQ ID NO:24) or (GVPGX)m (SEQ ID NO:25), wherein X is an amino acid except proline, and n or m is 1 or greater integer. X may be valine or alanine. n may be 1 to 12, and m may be 1 to 12. The ELP conjugated to a hydrophobic moiety may be stearoyl-(GVPGX)2-6 (SEQ ID NO:26). A carboxyl group at the carboxyl end of the stearoyl-(GVPGX)2-6 (SEQ ID NO:26) may be blocked or not. The blocking may be blocked by an amide bond formed between a carboxyl group and an amino group (example: forming —CO—NH$_2$).

The phospholipid derivative derivatized with a hydrophilic polymer may be DPPC-PEG or DSPE-PEG. The PEG may have a molecular weight of about 180 Da to about 50,000 Da.

The liposomes according to an embodiment may have a phase transition temperature of about 10° C. to about 70° C., for example, about 10° C. to about 60° C., about 10° C. to about 55° C., about 10° C. to about 45° C., about 20° C. to about 60° C., about 20° C. to about 55° C., about 30° C. to about 45° C., about 30° C. to about 45° C., about 35° C. to about 45° C. The phase transition temperature may be adjusted by length of a carbon chain of primary lipid, number of unsaturated bonds, mixtures of lipid, and combinations thereof. For example, when DSPC with a phase transition temperature higher than that of DPPC is mixed with DPPC with a lower phase transition temperature, liposomes composed of the DPPC and DSPC mixture may have a higher phase transition temperature than that of liposomes only composed of DPPC. The liposomes may be in a gel phase at room temperature.

The liposome according to an embodiment may further include at least one selected from the group consisting of a first active agent and a second active agent. The first active agent may be an anti-tumor agent. The first and/or second active agent may be entrapped within the liposome interior. The first and/or second active agent may be entrapped in the lipid bilayer of the liposome. Otherwise, the first and/or second active agent may be located on an outer surface of the liposome. The liposome may include both of the first and second active agent. The second active agent may be a diagnostic agent. The anti-tumor agent may be selected from the group consisting of methotrexate, doxorubicin, epirubicin, daunorubicin, vincristine, vinblastine, etoposide, ellipticine, camptothecin, paclitaxel, docetaxel, cisplatin, prednisone, methyl-prednisone, ibuprofen and a combination thereof. The diagnostic agent may be an imaging agent. The imaging agent may be diethylenetriaminepentaacetic acid-gadolinium (DTPA(Gd)). The imaging agent may be conjugated to a lipid of the lipid bilayer. For example, the imaging agent may be a phospholipid to which DTPA (Gd) is conjugated, for example DSPE-DTPA (Gd).

According to an embodiment, the liposome may include SA-V3-NH$_2$, DSPC+DPPC, DSPE-PEG and cholesterol; SA-V3-NH$_2$, DSPC+DPPC, DSPE-cRGDyK (SEQ ID NO:19), and cholesterol; SA-V3-NH$_2$, DSPC+DPPC, DSPE-cRGDyK (SEQ ID NO:19), DSPE-PEG and cholesterol; SA-V3-NH$_2$, DSPC+DPPC, DSPE-DTPA(Gd), DSPE-PEG and cholesterol; or SA-V3-NH$_2$, DSPC+DPPC, DSPE-cRGDyK (SEQ ID NO:19), DSPE-DTPA(Gd), DSPE-PEG and cholesterol. Otherwise the liposome may include SA-V3-NH$_2$, DPPC, DSPE-PEG and cholesterol; SA-V3-NH$_2$, DPPC, DSPE-cRGDyK (SEQ ID NO:19), and cholesterol; SA-V3-NH$_2$, DPPC, DSPE-cRGDyK (SEQ ID NO:19), DSPE-PEG and cholesterol; SA-V3-NH$_2$, DPPC, DSPE-DTPA(Gd), DSPE-PEG and cholesterol; or SA-V3-NH$_2$, DPPC, DSPE-cRGDyK (SEQ ID NO:19), DSPE-DTPA(Gd), DSPE-PEG and cholesterol. Here, SA is a stearoyl, and V represents VPGVG (SEQ ID NO:28).

According to another embodiment of the present invention, a pharmaceutical composition for delivering an active agent to a target site in a subject includes a pharmaceutically acceptable carrier or diluent, and a liposome. The liposome includes any one of or both of a first active agent and a second active agent; a lipid bilayer; an ELP conjugated to a hydrophobic moiety; and a lipid bilayer stabilizing agent, wherein the hydrophobic moiety may be packed in the lipid bilayer and the lipid bilayer includes the first lipid to which a tumor cell targeting material is bound.

The pharmaceutically acceptable carrier or diluent may be well known in the art. The carrier or diluent may be selected from the group consisting of water, for example saline or sterile water, Ringer's solution, buffered saline, dextrose solution, maltodextrose solution, glycerol, ethanol, and combinations thereof. The liposomes may be dispersed in an aqueous medium. The aqueous medium may include physiological saline or PBS.

The first and/or second active agent may be entrapped within the liposome interior. The first and/or second active agent may be entrapped in the lipid bilayer of the liposome. The first and/or second active agent may be located on an outer surface of the liposome. The liposome may have a phase transition temperature of about 39° C. to about 45° C. The liposome may be in a gel phase at room temperature. The liposome may include both of the first and second active agents. The second active agent may be a diagnostic agent. The first active agent may be an anti-tumor agent. The anti-tumor agent may be selected from the group consisting of methotrexate, doxorubicin, epirubicin, daunorubicin, vincristine, vinblastine, etoposide, ellipticine, camptothecin, paclitaxel, docetaxel, cisplatin, prednisone, methyl-prednisone, ibuprofen and a combination thereof. The diagnostic agent may be an imaging agent. The imaging agent may be diethylenetriaminepentaacetic acid-gadolinium (DTPA(Gd)). The imaging agent may be conjugated to a lipid of the lipid bilayer. For example, the imaging agent may be a phospholipid to which DTPA (Gd) is conjugated, for example DSPE-DTPA (Gd).

According to an embodiment, the liposome in the composition may include SA-V3-NH$_2$, DSPC+DPPC, DSPE-PEG and cholesterol; SA-V3-NH$_2$, DSPC+DPPC, DSPE-cRGDyK (SEQ ID NO:19), and cholesterol; SA-V3-NH$_2$, DSPC+DPPC, DSPE-cRGDyK (SEQ ID NO:19), DSPE-PEG and cholesterol; SA-V3-NH$_2$, DSPC+DPPC, DSPE-DTPA(Gd), DSPE-PEG and cholesterol; or SA-V3-NH$_2$, DSPC+DPPC, DSPE-cRGDyK, DSPE-DTPA(Gd), DSPE-PEG and cholesterol. Otherwise the liposome may include SA-V3-NH$_2$, DPPC, DSPE-PEG and cholesterol; SA-V3-NH$_2$, DPPC, DSPE-cRGDyK (SEQ ID NO:19), and cholesterol; SA-V3-NH$_2$, DPPC, DSPE-cRGDyK (SEQ ID NO:19), DSPE-PEG and cholesterol; SA-V3-NH$_2$, DPPC, DSPE-DTPA(Gd), DSPE-PEG and cholesterol; or SA-V3-NH$_2$, DPPC, DSPE-cRGDyK (SEQ ID NO:19), DSPE-DTPA(Gd), DSPE-PEG and cholesterol. Here, SA is a stearoyl, and V represents VPGVG (SEQ ID NO:28).

The subject may be a human or a mammal except a human. The mammal may be selected from the group consisting of a dog, a cat, a horse, a cow, a pig, a goat, a monkey, a mouse, and a combination thereof.

According to another embodiment of the present invention, a method of delivering an active agent to a target site in a subject includes administrating liposomes containing the active agent to a subject, wherein each liposome includes any one of or both of a first active agent, which are anti-tumor agent, and a second active agent a lipid bilayer, an ELP conjugated to a hydrophobic moiety, and a lipid bilayer stabilizing agent, the hydrophobic moiety is packed in the lipid bilayer, and the lipid bilayer includes a first lipid to which a tumor cell targeting material is bound; and heating the target site of a subject at least one point in time of before, at the same time, and after the administering to release the active agent from the liposomes at the target site.

The method includes administrating liposomes containing active agent to the subject. The liposomes containing the active agent have already been described above. Each liposome may have a phase transition temperature of from about 39° C. to about 45° C.

The administration may be parenteral administration. The parenteral administration, for example, may be intravenous, intradermal, intramuscular, intracavity (abdominal cavity, joints, or eye), or direct injection. The direct injection may involve injecting directly into a diseased site such as a tumor site. The liposomes may be administered intravenously and thereby brought to the target site such as a tumor site by blood flow. The target site may have a leaky property.

The method includes heating the target site of the subject at least one point in time of before, at the same time, and after the administering to release the active agent from the liposomes at the target site. The heating may be due to a clinical procedure that induces hyperthermia or may be related to an intrinsically higher temperature of an inflamed body part compared to the rest of the body. The clinical procedure that induces hyperthermia may be performed by direct heat transfer, for example, a hot liquid medium in a tub, e.g., contacting a body in water, irradiating ultrasound, e.g., high intensity ultrasound focused at a target site, applying a magnetic field, e.g., an amplified magnetic field, applying microwave and/or radiofrequency. The target site may be a region where pathological symptoms exist, for example, a tumor vasculature or a tumor site (i.e., a solid tumor). The heating may be heating to a temperature of about 39° C. to about 45° C.

The first and/or second active agent may be entrapped within the liposome interior. The first and/or second active agent may be entrapped in the lipid bilayer of the liposome. The first and/or second active agent may be located on an outer surface of the liposome. The liposome may have a phase transition temperature of about 39° C. to about 45° C. The liposome may be in a gel phase at room temperature. The liposome may include both of the first and second active agent. The second active agent may be a diagnostic agent. The first active agent may be an anti-tumor agent. The anti-tumor agent may be selected from the group consisting of methotrexate, doxorubicin, epirubicin, daunorubicin, vincristine, vinblastine, etoposide, ellipticine, camptothecin, paclitaxel, docetaxel, cisplatin, prednisone, methyl-prednisone, ibuprofen and a combination thereof. The diagnostic agent may be an imaging agent. The imaging agent may be diethylenetriaminepentaacetic acid-gadolinium (DTPA (Gd)). The imaging agent may be conjugated to a lipid of the lipid bilayer. The imaging agent may be conjugated to a phospholipid. For example, the imaging agent may be a phospholipid to which DTPA (Gd) is conjugated, for example DSPE-DTPA (Gd).

The method of which the second active agent is an imaging agent may further include detecting the second active agent after the administering and imaging a tumor vasculature region. The method may include specifically heating the tumor vasculature region based on the image of the tumor vasculature region obtained in the administering. The imaging may be performed by using a noninvasive method including magnetic resonance imaging (MRI), ultrasound, computed tomography (CT), laser, infrared ray, positron emission tomography (PET), and/or other imaging technologies. Also, the imaging may be performed by using a method using ultrasound or radiometer.

The permeability of liposomes, according to an embodiment, may be adjusted by shrinking and self-assembling of ELPs conjugated to a hydrophobic moiety depending on a temperature. Therefore, the liposome may be used as a vehicle for effectively delivering an active agent to a target site of a subject which is a tumor vasculature region.

The permeability of the liposomes containing active agent may be adjusted by a phase transition temperature of ELP conjugated to a hydrophobic moiety as well as a phase transition temperature of liposome itself. Thus, when the liposomes have a more stable composition at body temperature, for example, even at a status containing an effective amount of stabilizing molecules, such as cholesterol, for maintaining liposomes more stably at body temperature, the permeability may be efficiently adjusted by the phase transition temperature of ELP conjugated to a hydrophobic moiety.

According to a pharmaceutical composition for delivering active agent containing liposomes, according to another embodiment, to a subject, the composition may be used to efficiently deliver the active agent to the subject which is a tumor vasculature region.

According to a method of administering the active agent to the target sites in the body of the subject, according to another embodiment, the active agent may be efficiently delivered to the target sites in the body of the subject which is a tumor vasculature region.

The present invention will now be described more fully with respect to exemplary embodiments. The invention may, however, be embodied in many different forms and should not be construed as being limited to the embodiments set forth herein.

In Examples 1 to 9, liposomes not bound with a material specifically binding to a tumor vasculature was manufactured, and temperature sensitivity of the liposomes was confirmed. Also, in Examples 10 to 11, temperature sensitivity and imaging effect of liposomes, in which an imaging agent is mounted, were confirmed. In Examples 12 to 15, liposomes bound with a material specifically binding to a tumor vasculature was manufactured, temperature sensitivity of the liposomes was confirmed, and cellular uptake effect and cytotoxicity of the liposomes were confirmed.

Example 1: Preparation of Liposomes and Measurement of Thermal Sensitivity

Liposomes in a form of unilamellar vesicles were prepared using stearoyl-VPGVG VPGVG VPGVG-NH$_2$ (SEQ ID NO: 7), hereinafter referred to as "SA-V3-NH$_2$"), 1,2-dipalmitoyl-sn-glycero-3-phosphocholine (DPPC), [1,2-distearoyl-sn-glycero-3-phosphoethanolamine-N-[methoxy (polyethylene glycol)-2000] (ammonium salt)] (DSPE-PEG-2000), and cholesterol in a molar ratio of 0.55:55:2:10.

In detail, SA-V3-NH$_2$ was dissolved in methanol, and DPPC, DSPE-PEG and cholesterol were dissolved in chloroform. After mixing the methanol and chloroform solution in a round-bottom flask, a lipid thin layer was formed on the interior wall of the flask by evaporating the solvent at room temperature using a rotary evaporator.

Next, the liquid thin layer was hydrated by adding 250 mM of ammonium sulfate solution to the flask at room temperature.

A liposome solution of unilamella vesicle type liposomes was prepared by filtering the hydrated solution through a polycarbonate film with pores having a size of 100 nm. The prepared liposome solution was passed through a Sephadex G-50 column (GE Healthcare) filled with 25 mM Tris.HCl, and a liposome solution of liposomes with 250 mM of ammonium sulfate entrapped inside and 25 mM Tris.HCl on exterior surfaces was prepared. Then, doxorubicin (DOX) was added in a molar ratio of 1:0.2 to the main lipid component and incubated for an hour at a temperature of 37° C. The prepared liposome solution was passed through a Sephadex G-50 column (GE Healthcare) filled with physiological saline to remove untrapped DOX. As a result, liposomes with DOX entrapped in the aqueous interior were prepared (with an entrapping efficiency of 90% or higher). The prepared liposomes had an average diameter of 150 nm as measured by a Zeta-sizer instrument (Malvern inst.).

The in vitro stability and thermosensitivity of the prepared liposome formulations was assessed by measuring the percent release of DOX from the aqueous interior of the liposomes to the surrounding solution after 5 minutes of incubation at a temperature from about 25° C. to about 55° C. in the presence of physiological saline.

After incubation, the fluorescence intensity of the samples was measured at an excitation wavelength ($\lambda ex$)=488 nm and an emission wavelength ($\lambda em$)=612 nm after suitable dilutions to determine the amount of DOX released from the liposomes. The relative percent fluorescence intensity due to incubation at a particular temperature was calculated by comparison with the total release of entrapped material obtained after disruption of the liposome samples by adding 1% Triton X-100 (ethanol).

Example 2: Preparation of Liposomes and Measurement of Thermal Sensitivity

Liposomes with DOX entrapped in the aqueous interior were prepared in the same manner as in Example 1, except a DPPC/DSPC composition prepared with a molar ratio of 75/25 was used instead of DPPC. The prepared liposomes had an average diameter of about 170 nm as measured by a Zeta-sizer instrument (Malvern inst.).

Example 3: Preparation of Liposomes and Measurement of Thermal Sensitivity

Liposomes with DOX entrapped in the aqueous interior were prepared in the same manner as in Example 1, except a DPPC/DSPC composition prepared with a molar ratio of 50/50 was used instead of DPPC. The prepared liposomes had an average diameter of about 180 nm as measured by a Zeta-sizer instrument (Malvern inst.).

FIG. 1 is a graph showing the temperature release profiles of DOX from the liposomes prepared in Examples 1, 2, and 3 using SA-V3-NH$_2$, DPPC (or a mixture of DSPC+DPPC), DSPE-PEG, and cholesterol with a molar ratio of 0.55:55:2:10. As shown in FIG. 1, a temperature of the release of DOX was significantly increased when DPPC and DSPC were mixed. The maximum amount of release exceeded 70%. By mixing DPPC with a phase transition temperature of about 41° C. and DSPC with a phase transition temperature of about 54° C., a phase transition temperature of a liposome may be controlled, and thus a drug release temperature may be controlled.

Example 4: Preparation of Liposomes and Measurement of Thermal Sensitivity

Liposomes with DOX entrapped in the aqueous interior were prepared in the same manner as in Example 2, except a molar ratio of SA-V3-NH$_2$, DSPC+DPPC, DSPE-PEG, and cholesterol was 0.55:55:2:5. The prepared liposomes had an average diameter of about 170 nm as measured by a Zeta-sizer instrument (Malvern inst.).

Example 5: Preparation of Liposomes and Measurement of Thermal Sensitivity

Liposomes with DOX entrapped in the aqueous interior were prepared in the same manner as in Example 2, except a molar ratio of SA-V3-NH$_2$, DSPC+DPPC, DSPE-PEG, and cholesterol was 0.55:55:2:15. The prepared liposomes had an average diameter of about 170 nm as measured by a Zeta-sizer instrument (Malvern inst.).

Example 6: Preparation of Liposomes and Measurement of Thermal Sensitivity

Liposomes with DOX entrapped in the aqueous interior were prepared in the same manner as in Example 2, except a molar ratio of SA-V3-NH$_2$, DSPC+DPPC, DSPE-PEG, and cholesterol was 0.55:55:2:20. The prepared liposomes had an average diameter of about 170 nm as measured by a Zeta-sizer instrument (Malvern inst.).

Figure 2:
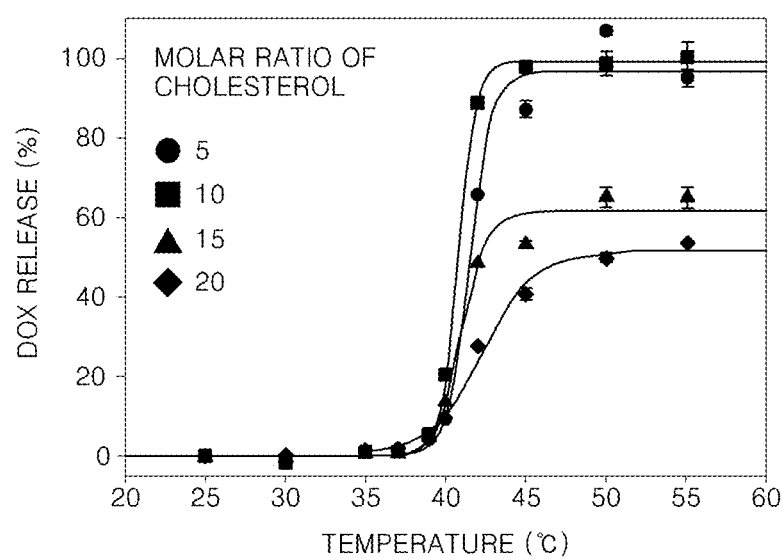
FIG. 2 is a graph showing temperature release profiles of DOX from liposomes prepared in Examples 4, 2, 5, and 6 using SA-V3-NH$_2$, DPPC/DSPC(75/25), DSPE-PEG, and cholesterol with a molar ratio of 0.55:55:2:5, 0.55:55:2:10, 0.55:55:2:15, 0.55:55:2:20, respectively.

FIG. 2 is a graph showing the temperature release profiles of DOX from the liposomes prepared in Examples 4, 2, 5, and 6 using SA-V3-NH$_2$, DPPC+DSPC, DSPE-PEG, and cholesterol with a molar ratio of 0.55:55:2:5, 0.55:55:2:10, 0.55:55:2:15, 0.55:55:2:20, respectively. As shown in FIG. 2, the maximum amount of drug release decreased as a content of cholesterol increased relative to a content of DPPC+DSPC at a temperature of 42° C. In this regard, it may be understood that cholesterol hinders phase transition of liposome membranes, which are formed of DPPC+DSPC. Therefore, it is confirmed that in order to implement 80% or more of drug release at a temperature of 42° C., a content of cholesterol relative to DPPC+DSPC has to be about 20% or less.

Example 7: Preparation of Liposomes and Measurement of Thermal Sensitivity

Liposomes with DOX entrapped in the aqueous interior were prepared in the same manner as in Example 2, except a molar ratio of SA-V3-NH$_2$, DSPC+DPPC, DSPE-PEG, and cholesterol was 0.275:55:2:10. The prepared liposomes had an average diameter of about 170 nm as measured by a Zeta-sizer instrument (Malvern inst.).

Example 8: Preparation of Liposomes and Measurement of Thermal Sensitivity

Liposomes with DOX entrapped in the aqueous interior were prepared in the same manner as in Example 2, except a molar ratio of SA-V3-NH$_2$, DSPC+DPPC, DSPE-PEG, and cholesterol was 1.1:55:2:10. The prepared liposomes had an average diameter of about 170 nm as measured by a Zeta-sizer instrument (Malvern inst.).

Example 9: Preparation of Liposomes and Measurement of Thermal Sensitivity

Liposomes with DOX entrapped in the aqueous interior were prepared in the same manner as in Example 2, except a molar ratio of SA-V3-NH$_2$, DSPC+DPPC, DSPE-PEG, and cholesterol was 2.75:55:2:10. The prepared liposomes had an average diameter of about 170 nm as measured by a Zeta-sizer instrument (Malvern inst.).

Figure 3:
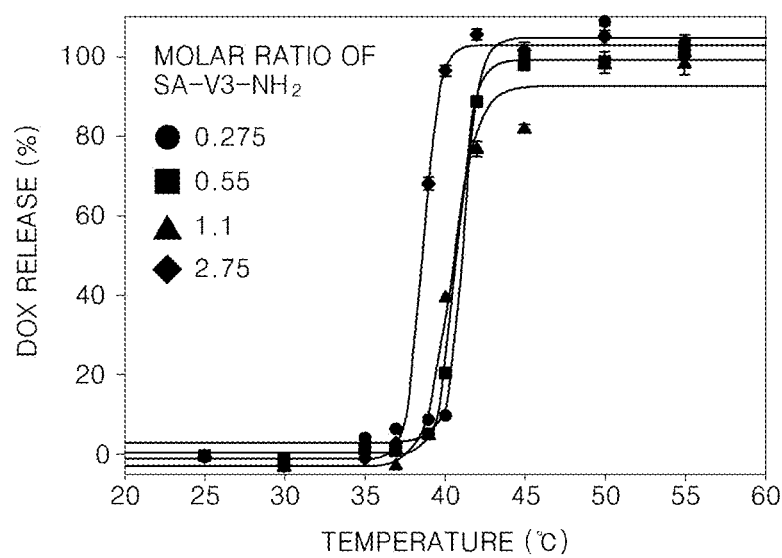
FIG. 3 is a graph showing temperature release profiles of DOX from liposomes prepared in Examples 7, 2, 8, and 9 using SA-V3-NH$_2$, DPPC/DSPC(75/25), DSPE-PEG, and cholesterol with a molar ratio of 0.275:55:2:10, 0.55:55:2:10, 1.1:55:2:10, 2.75:55:2:10, respectively.

FIG. 3 is a graph showing the temperature release profiles of DOX from the liposomes prepared in Examples 7, 2, 8, and 9 using SA-V3-NH$_2$, DPPC+DSPC, DSPE-PEG, and cholesterol with a molar ratio of 0.275:55:2:10, 0.55:55:2:10, 1.1:55:2:10, 2.75:55:2:10, respectively. As shown in FIG. 3, the maximum amount of drug release was 80% or more regardless of a content of SA-V3-NH$_2$ relative to a content of DPPC+DSPC at a temperature of 42° C. In this regard, it is confirmed that a content of SA-V3-NH$_2$ is not related to a maximum amount of drug release. However, when SA-V3-NH$_2$, DSPC+DPPC, DSPE-PEG, and cholesterol in the liposomes had a molar ratio of 2.75:55:2:10 as in Example 9, an initial temperature of drug release was decreased by about 2° C. to about 3° C. It may be understood that the temperature decrease was due to interactions between SA-V3-NH$_2$ molecules inserted in the liposomes, but is not limited to any particular mechanism.

Example 10: Preparation of Liposomes Having Imaging Agent

Liposomes with DOX entrapped in the aqueous interior were prepared in the same manner as in Example 2, except DPPC/DSPC/DSPE-DTPA(Gd) was used with a molar ratio of 75/24/1 instead of DSPC/DPPC. The prepared liposomes had an average diameter of about 170 nm as measured by a Zeta-sizer instrument (Malvern inst.).

amount of drug release was 80% or more at a temperature of 42° C. In this regard, it is confirmed that liposomes having DSPE-DTPA(Gd), which is an imaging agent of MRI, demonstrate temperature-sensitive drug release.

Figure 5:
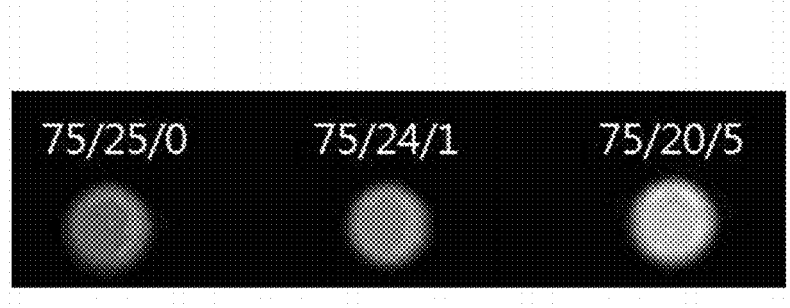
FIG. 5 is MRI T1 weighted images showing liposomes prepared in Examples 2, 10, and 11 using SA-V3-NH$_2$ DPPC/DSPC/DSPE-DTPA(Gd) (75/25/0 or 75/24/1 or 75/20/5), DSPE-PEG, and cholesterol with a molar ratio of 0.55:55:2:10.

FIG. 5 is MRI T1 weighted images showing the liposomes prepared in Examples 2, 10 and 11 using SA-V3-NH$_2$ DPPC+DSPC+DSPE-DTPA(Gd), DSPE-PEG, and cholesterol with a molar ratio of 0.55:55:2:10. As shown in FIG. 5, it was confirmed that T1 weighted image was shown brighter as a content of DSPE-DTPA(Gd) in the liposomes prepared using DPPC/DSPC/DSPE-DTPA(Gd) with molar ratios of DPPC/DSPC/DSPE-DTPA(Gd) 75/25 (Example 2), 75/24/1 (Example 10), and 75/20/5 (Example 11). In this regard, it is confirmed that DSPE-DTPA(Gd) in the liposomes enable MRI.

Example 12: Preparation of Liposomes Having Tumor Vasculature Targeting cRGD

Liposomes with DOX entrapped in the aqueous interior were prepared in the same manner as in Example 2, except DSPE-PEG-cRGD was used instead of DSPE-PEG. The prepared liposomes had an average diameter of about 170 nm as measured by a Zeta-sizer instrument (Malvern inst.). DSPE-PEG-cRGD used in the current embodiment was DSPE-PEG2000-cRGDNa+, which has Formula 5 below, wherein R$_1$ is —C(O)—[OCH$_2$CH$_2$]$_n$—O(CH$_2$)$_3$—NH—C(O)—(CH$_2$)$_3$—C(O)— and —[OCH$_2$CH$_2$]$_n$— has a molecular weight of about 2,000 Da.

(Formula 5)

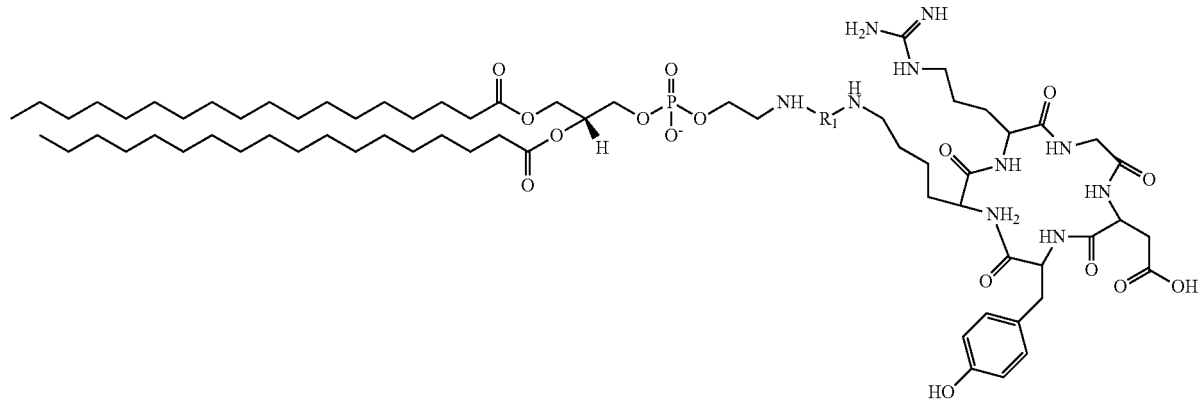

Example 11: Preparation of Liposomes Having Imaging Agent

Liposomes with DOX entrapped in the aqueous interior were prepared in the same manner as in Example 2, except DPPC/DSPC/DSPE-DTPA(Gd) was used with a molar ratio of 75/20/5 instead of DSPC/DPPC. The prepared liposomes had an average diameter of about 170 nm as measured by a Zeta-sizer instrument (Malvern inst.).

Figure 4:
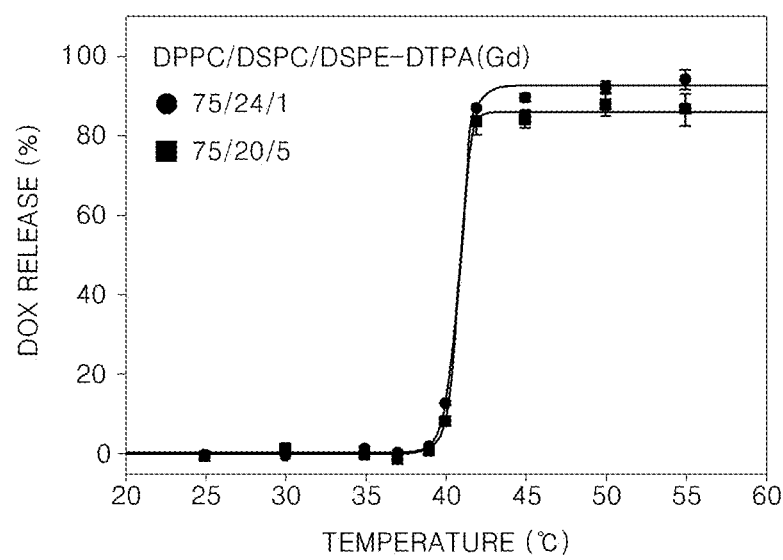
FIG. 4 is a graph showing temperature release profiles of DOX from liposomes prepared in Examples 10 and 11 using SA-V3-NH$_2$ DPPC/DSPC/DSPE-DTPA(Gd) (75/24/1 or 75/20/5), DSPE-PEG, and cholesterol with a molar ratio of 0.55:55:2:10.
Figure 6:
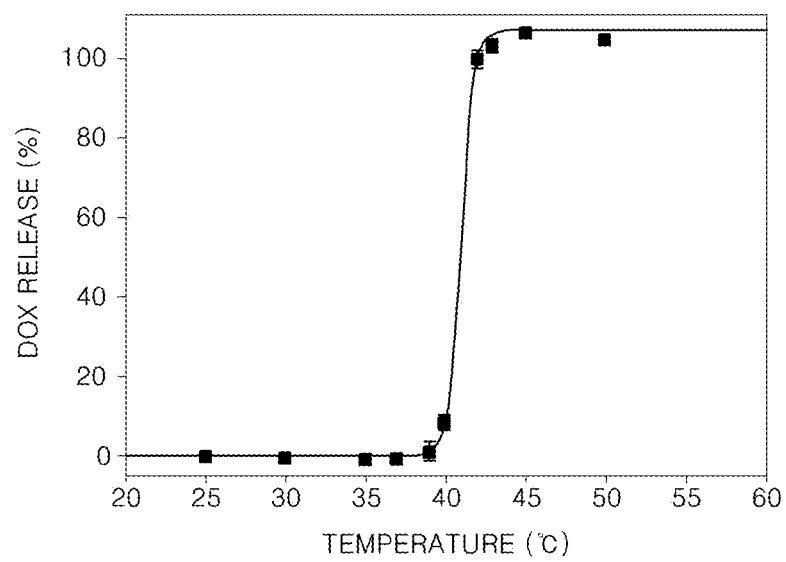
FIG. 6 is a graph showing temperature-sensitive drug release behavior of liposomes prepared in Example 12 using SA-V3-NH$_2$ DPPC/DSPC (75/25), DSPE-PEG-cRGD, and cholesterol with a molar ratio of 0.55:55:2:10.

FIG. 4 is a graph showing the temperature release profiles of DOX from the liposomes prepared in Examples 10 and 11 using SA-V3-NH$_2$ DPPC+DSPC+DSPE-DTPA(Gd), DSPE-PEG, and cholesterol with a molar ratio of 0.55:55:2:10. As shown in FIG. 4, drug release behaviors of the liposomes that were prepared using DPPC/DSPC/DSPE-DTPA(Gd) with molar ratios of 75/24/1 (Example 10) and 75/20/5 (Example 11) appeared similarly. The maximum FIG. 6 is a graph showing temperature-sensitive drug release behavior of the liposomes prepared in Example 12 using SA-V3-NH$_2$ DPPC+DSPC, DSPE-PEG-cRGD, and cholesterol with a molar ratio of 0.55:55:2:10. As shown in FIG. 6, it was confirmed that the liposomes having DSPE-PEG-cRGD, which is a targeting material, demonstrated 80% or more of drug release at a temperature of 42° C.

Example 13: Tumor Targeting Characteristics of Liposomes Having cRGD

In order to confirm tumor targeting characteristics of temperature-sensitive liposomes modified with cRGD, cellular uptake effect of U-87MG cells (Human glioblastoma-astrocytoma, epithelial-like cell line), on which αvβ$_3$ integrin with high binding affinity to cRGD is over-expressed, and KB cells, on which αvβ$_3$ integrin is not over-expressed, was confirmed. Also, in order to confirm influence of cRGD modification, the DOX-entrapped liposomes prepared in Examples 2 (not modified with cRGD) and 12 (modified with cRGD) were used.

U-87MG cells, on which $\alpha v \beta_3$ integrin with high binding affinity to cRGD is over-expressed, were grown in 6-well with a distribution of $5.0 \times 10^4$ cells/well in 2 mL of Minimum Essential Medium Eagle (MEM) including 10% of Fetal bovine serum (FBS) for 24 hours. The liposomes prepared in Examples 2 and 12 were treated with a concentration of 30 μg/mL of DOX concentration and maintained at a temperature of 37° C. for 2 hours. After MEM was removed, the cells were washed with saline solution including 1% of bovine serum albumin (BSA) and filled with new MEM. After maintained at a temperature of 37° C. and 42° C. for 30 minutes, MEM was removed, and the cells were washed with saline solution including 1% of BSA. The cells were removed from the well using cell dissociation solution (Sigma Aldrich), and fluorescence activated cell sorting (FACS) was performed to detect the cells.

FACS was performed in the same manner as to prepare U-87MG, except KB cells, on which $\alpha v \beta_3$ integrin is not over-expressed, were grown in RPMI1640 media including 10% of FBS to compare to the cellular uptake of U-87MG.

Figure 7:
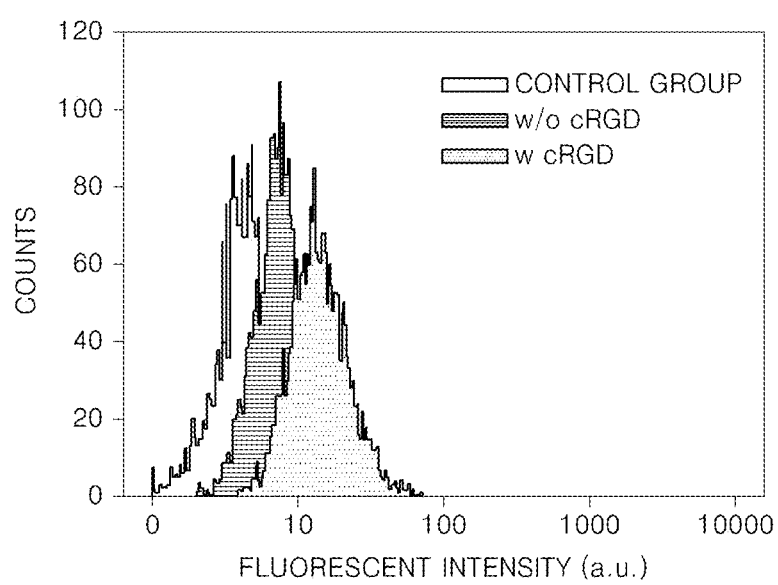
FIG. 7 is a graph showing the result of in vitro FACS of U-87MG cells performed according to Example 13.
Figure 8:
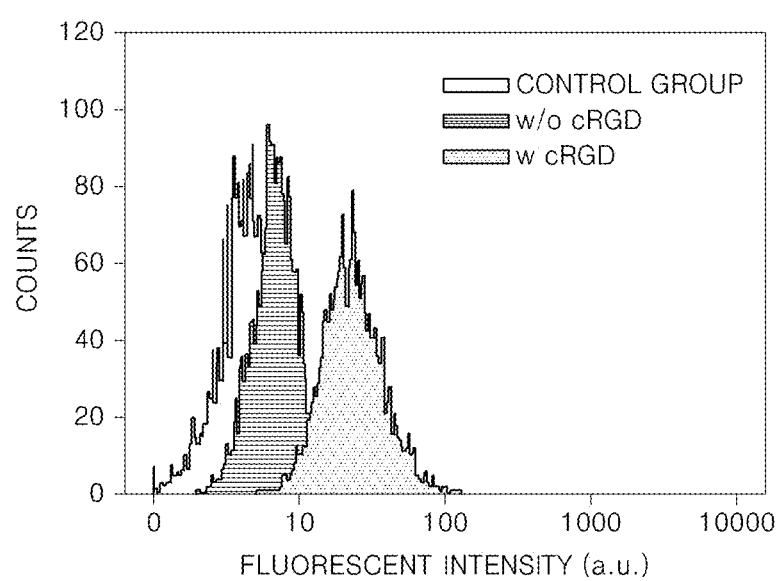
FIG. 8 is a graph showing the result of in vitro FACS of U-87MG cells performed according to Example 13.

FIGS. 7, 8, 9, and 10 show results of FACS measurement of U-87MG and KB cells. As shown in FIG. 7, when the cells were treated at a temperature of 37° C., it was confirmed that relatively more quantity of the liposomes of Example 12 having cRGD was delivered into the cells than the liposomes of Example 2 not having cRGD. Also, when the cells were treated at a temperature of 42° C., as shown in FIG. 8, it may be known that the cells have a higher fluorescence value. When the cells were treated at a temperature of 42° C., fluorescence of DOX increased due to the drug release from the liposomes releasing, thereby increasing the overall fluorescence value.

Figure 9:
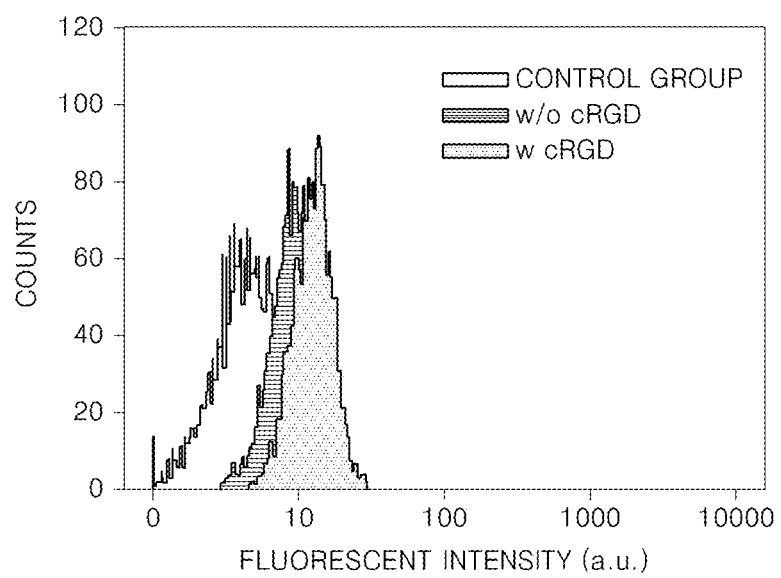
FIG. 9 is a graph showing the result of in vitro FACS of KB cells performed according to Example 13.
Figure 10:
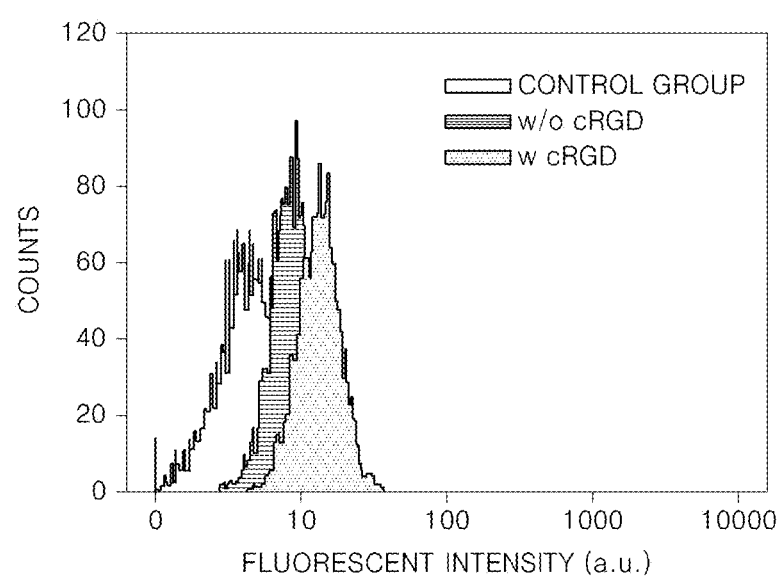
FIG. 10 is a graph showing the result of in vitro FACS of KB cells performed according to Example 13.

FIGS. 9 and 10 show targeting effect of KB cells, on which $\alpha v \beta_3$ integrin is not over-expressed. Although the liposomes modified with cRGD (Example 12) showed a slight higher fluorescence compared to the liposomes not modified with cRGD (Example 2), not more quantity of the liposomes modified with cRGD (Example 12) were delivered into the cells compared to U-87MG.

It was confirmed that cRGD modification enabled drug to be selectively delivered to cells on which $\alpha v \beta_3$ integrin is over-expressed by confirming cellular uptake effect of U-87MG and KB cells.

Example 14: Tumor Targeting Characteristics of Liposomes Having cRGD (Cellular Uptake, Confocal Microscopy)

In order to confirm tumor targeting characteristics of temperature-sensitive liposomes modified with cRGD, cellular uptake effect of U-87MG on which $\alpha v \beta_3$ integrin with high binding affinity to cRGD is over-expressed was confirmed by using a confocal microscopy. Also, in order to confirm influence of cRGD modification, the DOX-entrapped liposomes prepared in Examples 2 (not modified with cRGD) and 12 (modified with cRGD) were used.

U-87MG cells, on which $\alpha v \beta_3$ integrin binding with cRGD is over-expressed, were grown in 96-well with a distribution of $5 \times 10^3$ cells/well in 100 μL of MEM including 10% of FBS for 24 hours. The liposomes prepared in Example 2 or 12 were treated with a concentration of 30 μg/mL of DOX concentration and maintained at a temperature of 37° C. for 1 hour. After MEM was removed, the cells were washed with saline solution including 1% of BSA and filled with new MEM. After maintained at a temperature of 42° C. for 30 minutes, MEM was removed, and the cells were washed with saline solution including 1% of BSA. Images of the cells were observed using IN CELL ANALYZER (GE healthcare).

Figure 11:
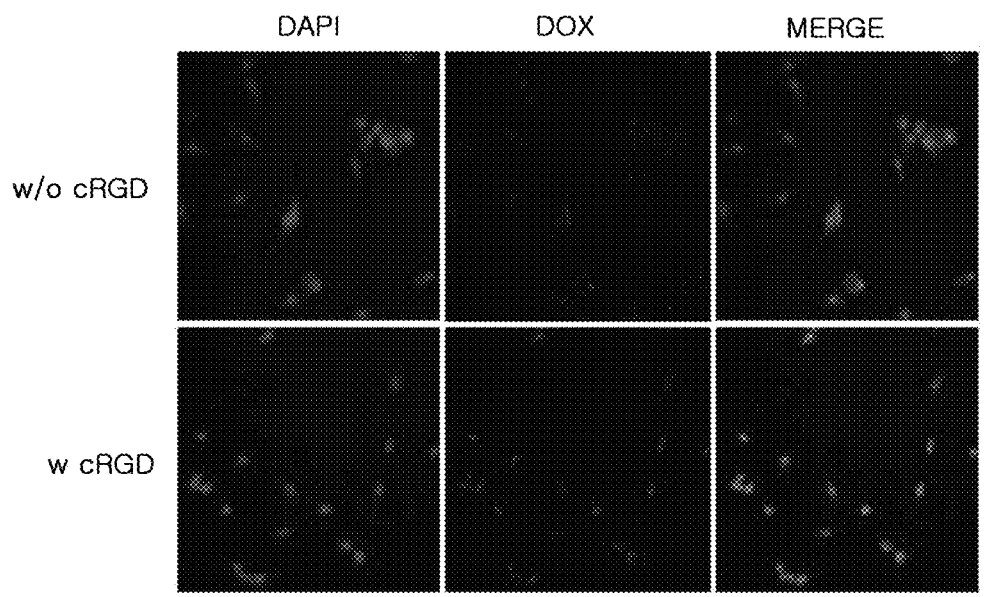
FIG. 11 is an image showing a result of confocal microscopy observation of U-87MG cells performed according to Example 14.

FIG. 11 shows results of observation in U-87MG cells. In FIG. 11, it may be confirmed that relatively more quantity of the liposomes of Example 12 having cRGD was delivered into the cells than the liposomes of Example 2 not having cRGD.

It was confirmed that cRGD modification enabled drug to be selectively delivered to cells on which $\alpha v \beta_3$ integrin is over-expressed by confirming cellular uptake effect of U-87MG.

Example 15: Tumor Targeting Characteristics of Liposomes Having cRGD (Cellular Toxicity)

In order to confirm tumor targeting characteristics of temperature-sensitive liposomes modified with cRGD, toxicity of cellular uptake effect of U-87MG on which $\alpha v \beta_3$ integrin with high binding affinity to cRGD is over-expressed was confirmed.

U-87MG cells, on which $\alpha v \beta_3$ integrin binding with cRGD is over-expressed, were grown in 96-well with a distribution of $5 \times 10^5$ cells/well in 100 μL of MEM including 10% of FBS for 24 hours. The liposomes prepared in Example 2 or 12 were treated with a concentration of 30 μg/mL of DOX concentration and maintained at a temperature of 37° C. for 1 hour. After MEM was removed, the cells were washed with saline solution including 1% of BSA and filled with new MEM. After maintained at a temperature of 37° C. and 42° C. for 30 minutes. After maintained at a temperature of 37° C. for two days, toxicity of treated drug and the liposomes were confirmed using WST-1 analysis.

Figure 12:
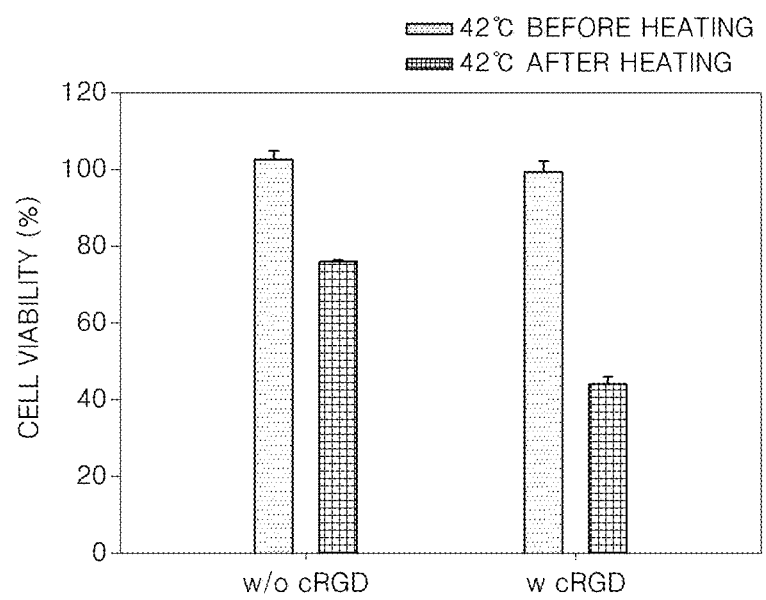
FIG. 12 is a graph showing cell toxicity of temperature sensitive liposomes having cRGD performed according to Example 15.

FIG. 12 shows cell toxicity of liposomes. Most of the cells survived when the liposomes treated at a temperature of 37° C. prepared in Example 2 were used, but about 75% of cells survived when the liposomes treated at a temperature of 42° C. prepared in Example 2 were used. This indicates that the liposomes partially delivered into the cells by diffusion do not release drug at a temperature of 37° C. but release drug at a temperature of 42° C. and thus toxicity was shown at a temperature of 42° C., but is not limited to any particular mechanism. However, although the liposomes modified with cRGD prepared in Example 11 were delivered a lot into the cells by receptor mediated endocytosis, toxicity was not shown since drug was not released at a temperature of 37° C. and showed about 40% of cell viability due to drug release when the liposomes were treated at a temperature of 42° C. This accord with FACS results of FIG. 10, thereby confirming that intracellular drug delivery may be increased by having cRGD It should be understood that the exemplary embodiments described therein should be considered in a descriptive sense only and not for purposes of limitation. Descriptions of features or aspects within each embodiment should typically be considered as available for other similar features or aspects in other embodiments.

What is claimed is:

1. A liposome comprising:
   a lipid bilayer;
   an elastin-like polypeptide (ELP) conjugated to a hydrophobic moiety, wherein the hydrophobic moiety is in the lipid bilayer; and
   a lipid bilayer stabilizing agent comprising cholesterol, a fatty acid ester of cholesterol, sitosterol, ergosterol, stigmasterol, 4,22-stigmastadien-3-one, stigmasterol acetate, lanosterol, or a combination thereof;
   wherein the lipid bilayer comprises a DSPE-cRGDyK molecule having Formula 5 below, salts thereof, stereoisomer thereof, or a combination thereof:

(Formula 5)

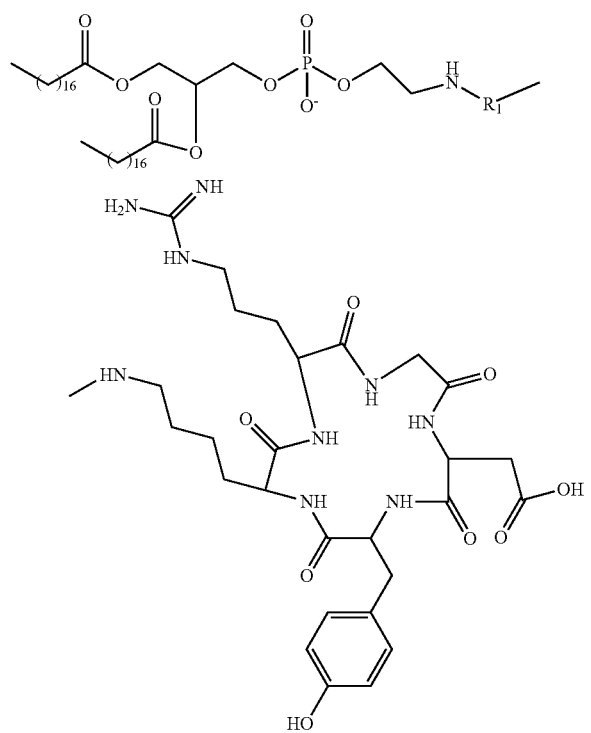

wherein $R_1$ is —C(O)—($R_2$)—C(O)— and $R_2$ is C1-C50 alkylene, or $R_2$ is a PEG moiety comprising —[OCH$_2$CH$_2$]n-, wherein n is an integer of 1 to 1,000.

2. The liposome of claim 1, wherein the ELP comprises repeating units of VPGXG (SEQ ID NO: 1), PGXGV (SEQ ID NO: 2), GXGVP (SEQ ID NO: 3), XGVPG (SEQ ID NO: 4), GVPGX (SEQ ID NO: 5) or a combination thereof, wherein V is valine, P is proline, G is glycine, and X is any amino acid except proline.

3. The liposome of claim 1, wherein the hydrophobic moiety conjugated to the ELP is a saturated or unsaturated hydrocarbon group, a saturated or unsaturated acyl group, or a saturated or unsaturated alkoxy group.

4. The liposome of claim 1, wherein the lipid bilayer further comprises a phospholipid derivatized with a hydrophilic polymer, wherein the hydrophilic polymer is polyethylene glycol (PEG), polylactic acid, polyglycolic acid, a copolymer of polylactic acid and polyglycolic acid, polyvinyl alcohol, polyvinyl pyrrolidone, oligosaccharide, or a combination thereof.

5. The liposome of claim 1, wherein the liposome has a phase transition temperature of about 39° C. to about 45° C.

6. The liposome of claim 1, wherein the liposome has a diameter in a range of about 50 nm to about 500 nm.

7. The liposome of claim 1, wherein the liposome further comprises at least one active agent.

8. The liposome of claim 7, wherein the active-agent is an anti-tumor agent.

9. A liposome comprising a lipid bilayer;
   an elastin-like polypeptide (ELP) conjugated to a hydrophobic moiety, wherein the hydrophobic moiety is in the lipid bilayer; and
   a lipid bilayer stabilizing agent comprising cholesterol, a fatty acid ester of cholesterol, sitosterol, ergosterol, stigmasterol, 4,22-stigmastadien-3-one, stigmasterol acetate, lanosterol, or a combination thereof;
   wherein the lipid bilayer comprises a DSPE-cRGDyK molecule having Formula 5 below, salts thereof, stereoisomer thereof, or a combination thereof:

(Formula 5)

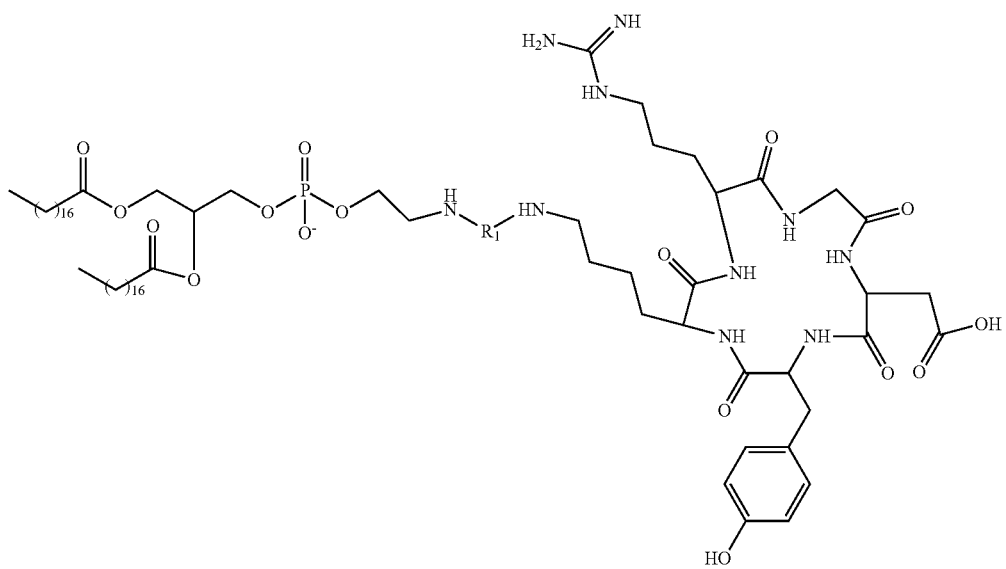

wherein $R_1$ is —C(O)—($R_2$)—C(O)— and $R_2$ is C1-C50 alkylene, or $R_2$ is a PEG moiety comprising —[OCH$_2$CH$_2$]n-, wherein n is an integer of 1 to 1,000, wherein the liposome comprises SA-V3-NH$_2$, DSPC+DPPC, DSPE-PEG and cholesterol;

SA-V3-NH$_2$, DSPC+DPPC, DSPE-PEG-cRGDyK (SEQ ID NO:21), and cholesterol;

SA-V3-NH$_2$, DSPC+DPPC, DSPE-PEG-cRGDyK (SEQ ID NO:21), DSPE-PEG and cholesterol;

SA-V3-NH$_2$, DSPC+DPPC, DSPE-DTPA(Gd), DSPE-PEG and cholesterol;

SA-V3-NH$_2$, DSPC+DPPC, DSPE-PEG-cRGDyK (SEQ ID NO:21), DSPE-DTPA(Gd), DSPE-PEG and cholesterol;

SA-V3-NH$_2$, DPPC, DSPE-PEG and cholesterol;

SA-V3-NH$_2$, DPPC, DSPE-PEG-cRGDyK (SEQ ID NO:21), and cholesterol;

SA-V3-NH$_2$, DPPC, DSPE-PEG-cRGDyK (SEQ ID NO:21), DSPE-PEG and cholesterol;

SA-V3-NH$_2$, DPPC, DSPE-DTPA(Gd), DSPE-PEG and cholesterol; or

SA-V3-NH$_2$, DPPC, DSPE-PEG-cRGDyK (SEQ ID NO:21), DSPE-DTPA(Gd), DSPE-PEG and cholesterol, wherein DSPE-PEG-cRGDyK is the DSPE-cRGDyK molecule wherein $R_2$ is the PEG moiety comprising —[OCH$_2$CH$_2$]$_n$—.

10. A pharmaceutical composition for delivering an active agent to a subject comprising:
the liposome of claim 7; and
a pharmaceutically acceptable carrier or diluent.

11. The composition of claim 10, wherein the ELP comprises repeating units of VPGXG (SEQ ID NO: 1), PGXGV (SEQ ID NO: 2), GXGVP (SEQ ID NO: 3), XGVPG (SEQ ID NO: 4), GVPGX (SEQ ID NO: 5) or a combination thereof, wherein V is valine, P is proline, G is glycine, and X is any amino acid except proline.

12. The composition of claim 10, wherein the liposome has a phase transition temperature of about 39° C. to about 45° C.

13. The composition of claim 10, wherein the liposome has a diameter of about 50 nm to about 500 nm.

14. The composition of claim 10, wherein the hydrophobic moiety conjugated to the ELP is a saturated or unsaturated hydrocarbon group, a saturated or unsaturated acyl group, or a saturated or unsaturated alkoxy group.

15. A pharmaceutical composition for delivering an active agent to a subject comprising:
the liposome of claim 7; and
a pharmaceutically acceptable carrier or diluent, wherein the liposome comprises SA-V3-NH$_2$, DSPC+DPPC, DSPE-PEG and cholesterol;

SA-V3-NH$_2$, DSPC+DPPC, DSPE-PEG-cRGDyK (SEQ ID NO:21), and cholesterol;

SA-V3-NH$_2$, DSPC+DPPC, DSPE-PEG-cRGDyK (SEQ ID NO:21), DSPE-PEG and cholesterol;

SA-V3-NH$_2$, DSPC+DPPC, DSPE-DTPA(Gd), DSPE-PEG and cholesterol;

SA-V3-NH$_2$, DSPC+DPPC, DSPE-PEG-cRGDyK (SEQ ID NO:21), DSPE-DTPA(Gd), DSPE-PEG and cholesterol;

SA-V3-NH$_2$, DPPC, DSPE-PEG and cholesterol;

SA-V3-NH$_2$, DPPC, DSPE-PEG-cRGDyK (SEQ ID NO:21), and cholesterol;

SA-V3-NH$_2$, DPPC, DSPE-PEG-cRGDyK (SEQ ID NO:21), DSPE-PEG and cholesterol;

SA-V3-NH$_2$, DPPC, DSPE-DTPA(Gd), DSPE-PEG and cholesterol; or

SA-V3-NH$_2$, DPPC, DSPE-PEG-cRGDyK (SEQ ID NO:21), DSPE-DTPA(Gd), DSPE-PEG and cholesterol, wherein DSPE-PEG-cRGDyK is the DSPE-cRGDyK molecule wherein $R_2$ is the PEG moiety comprising —[OCH$_2$CH$_2$]$_n$—.

16. A method of delivering an active agent to a target site in a subject, the method comprising:
administering the pharmaceutical composition of claim 10 to the subject, wherein the active agent is an anti-tumor agent; and
heating the target site of the subject to release the active agent from the liposome at the target site.

17. The method of claim 16, wherein the ELP comprises repeating units of VPGXG (SEQ ID NO: 1), PGXGV (SEQ ID NO: 2), GXGVP (SEQ ID NO: 3), XGVPG (SEQ ID NO: 4), GVPGX (SEQ ID NO: 5) or a combination thereof, wherein V is valine, P is proline, G is glycine, and X is any amino acid except proline.

18. The method of claim 16, wherein the liposome has a phase transition temperature of about 39° C. to about 45° C.

19. The method of claim 16, wherein the heating is heating to a temperature of about 39° C. to about 45° C.

\* \* \* \* \*

SEQUENCE LISTING

<160> NUMBER OF SEQ ID NOS: 28

<210> SEQ ID NO 1
<211> LENGTH: 5
<212> TYPE: PRT
<213> ORGANISM: Artificial Sequence
<220> FEATURE:
<223> OTHER INFORMATION: Synthetic elastin-like polypeptide unit
      sequence
<220> FEATURE:
<221> NAME/KEY: VARIANT
<222> LOCATION: (4)
<223> OTHER INFORMATION: Xaa denotes amino acid other than proline

<400> SEQUENCE: 1

Val Pro Gly Xaa Gly
 1               5

<210> SEQ ID NO 2
<211> LENGTH: 5
<212> TYPE: PRT
<213> ORGANISM: Artificial Sequence
<220> FEATURE:
<223> OTHER INFORMATION: Synthetic elastin-like polypeptide unit
      sequence
<220> FEATURE:
<221> NAME/KEY: VARIANT
<222> LOCATION: (3)
<223> OTHER INFORMATION: Xaa denotes amino acid other than proline

<400> SEQUENCE: 2

Pro Gly Xaa Gly Val
 1               5

<210> SEQ ID NO 3
<211> LENGTH: 5
<212> TYPE: PRT
<213> ORGANISM: Artificial Sequence
<220> FEATURE:
<223> OTHER INFORMATION: Synthetic elastin-like polypeptide unit
      sequence
<220> FEATURE:
<221> NAME/KEY: VARIANT
<222> LOCATION: (2)
<223> OTHER INFORMATION: Xaa denotes amino acid other than proline

<400> SEQUENCE: 3

Gly Xaa Gly Val Pro
 1               5

<210> SEQ ID NO 4
<211> LENGTH: 5
<212> TYPE: PRT
<213> ORGANISM: Artificial Sequence
<220> FEATURE:
<223> OTHER INFORMATION: Synthetic elastin-like polypeptide unit
      sequence
<220> FEATURE:
<221> NAME/KEY: VARIANT
<222> LOCATION: (1)
<223> OTHER INFORMATION: Xaa denotes amino acid other than proline

<400> SEQUENCE: 4

Xaa Gly Val Pro Gly
 1               5

<210> SEQ ID NO 5
<211> LENGTH: 5
<212> TYPE: PRT
<213> ORGANISM: Artificial Sequence

```
<220> FEATURE:
<223> OTHER INFORMATION: Synthetic elastin-like polypeptide unit
      sequence
<220> FEATURE:
<221> NAME/KEY: VARIANT
<222> LOCATION: (5)
<223> OTHER INFORMATION: Xaa denotes amino acid other than proline

<400> SEQUENCE: 5

Gly Val Pro Gly Xaa
  1               5

<210> SEQ ID NO 6
<211> LENGTH: 30
<212> TYPE: PRT
<213> ORGANISM: Artificial Sequence
<220> FEATURE:
<223> OTHER INFORMATION: Synthetic elastin-like polypeptide unit
      sequence modified with stearoylation and amidation
<220> FEATURE:
<221> NAME/KEY: VARIANT
<222> LOCATION: (1)
<223> OTHER INFORMATION: Amino terminal nitrogen is stearoylated
<220> FEATURE:
<221> NAME/KEY: VARIANT
<222> LOCATION: (30)
<223> OTHER INFORMATION: Carboxy terminal carboxy group is amidated
      with -NH2
<220> FEATURE:
<221> NAME/KEY: VARIANT
<222> LOCATION: (1)..(30)
<223> OTHER INFORMATION: X within the sequence denotes amino acids
      other than proline.

<400> SEQUENCE: 6

Val Pro Gly Xaa Gly Val Pro Gly Xaa Gly Val Pro Gly Xaa Gly Val
  1               5                  10                  15

Pro Gly Xaa Gly Val Pro Gly Xaa Gly Val Pro Gly Xaa Gly
             20                  25                  30

<210> SEQ ID NO 7
<211> LENGTH: 15
<212> TYPE: PRT
<213> ORGANISM: Artificial Sequence
<220> FEATURE:
<223> OTHER INFORMATION: Synthetic elastin-like polypeptide unit
      sequence modified with stearoylation at amino terminal and
      amidation at carboxy terminal
<220> FEATURE:
<221> NAME/KEY: VARIANT
<222> LOCATION: (1)
<223> OTHER INFORMATION: Amino terminal nitrogen is stearoylated
<220> FEATURE:
<221> NAME/KEY: VARIANT
<222> LOCATION: (15)
<223> OTHER INFORMATION: Carboxy terminal carboxyl group is
      amidated with -NH2

<400> SEQUENCE: 7

Val Pro Gly Val Gly Val Pro Gly Val Gly Val Pro Gly Val Gly
  1               5                  10                  15

<210> SEQ ID NO 8
<211> LENGTH: 7
<212> TYPE: PRT
<213> ORGANISM: Artificial Sequence
<220> FEATURE:
<223> OTHER INFORMATION: Synthetic Isolated peptide homing to
      malignant pancreatic vasculature
```

```
<400> SEQUENCE: 8

Cys Arg Gly Arg Arg Ser Thr
  1               5

<210> SEQ ID NO 9
<211> LENGTH: 6
<212> TYPE: PRT
<213> ORGANISM: Artificial Sequence
<220> FEATURE:
<223> OTHER INFORMATION: Synthetic Isolated peptide homing to
      malignant pancreatic vasculature

<400> SEQUENCE: 9

Cys Arg Ser Arg Lys Gly
  1               5

<210> SEQ ID NO 10
<211> LENGTH: 7
<212> TYPE: PRT
<213> ORGANISM: Artificial Sequence
<220> FEATURE:
<223> OTHER INFORMATION: Synthetic Isolated peptide homing to
      malignant pancreatic vasculature

<400> SEQUENCE: 10

Cys Lys Ala Ala Lys Asn Lys
  1               5

<210> SEQ ID NO 11
<211> LENGTH: 5
<212> TYPE: PRT
<213> ORGANISM: Artificial Sequence
<220> FEATURE:
<223> OTHER INFORMATION: synthetic cyclic peptide
<220> FEATURE:
<221> NAME/KEY: VARIANT
<222> LOCATION: (4)
<223> OTHER INFORMATION: Tyr is D-tyrosine.

<400> SEQUENCE: 11

Arg Gly Asp Tyr Lys
  1               5

<210> SEQ ID NO 12
<211> LENGTH: 7
<212> TYPE: PRT
<213> ORGANISM: Artificial Sequence
<220> FEATURE:
<223> OTHER INFORMATION: Synthetic cyclic peptide
<220> FEATURE:
<221> NAME/KEY: VARIANT
<222> LOCATION: (2)
<223> OTHER INFORMATION: Xaa is any amino acid.
<220> FEATURE:
<221> NAME/KEY: VARIANT
<222> LOCATION: (6)
<223> OTHER INFORMATION: Xaa is any amino acid
<220> FEATURE:
<221> NAME/KEY: VARIANT
<222> LOCATION: (7)
<223> OTHER INFORMATION: Xaa is an amino acid that may form a ring
      together with a cysteine residue
<220> FEATURE:
<221> NAME/KEY: NON_CONS
<222> LOCATION: (2)..(3)
<220> FEATURE:
<221> NAME/KEY: NON_CONS
<222> LOCATION: (6)..(7)
```

```
<400> SEQUENCE: 12

Cys Xaa Arg Gly Asp Xaa Xaa
 1               5

<210> SEQ ID NO 13
<211> LENGTH: 8
<212> TYPE: PRT
<213> ORGANISM: Artificial Sequence
<220> FEATURE:
<223> OTHER INFORMATION: synthetic cyclic peptide
<220> FEATURE:
<221> NAME/KEY: VARIANT
<222> LOCATION: (8)
<223> OTHER INFORMATION: Xaa is any amino acid
<220> FEATURE:
<221> NAME/KEY: NON_CONS
<222> LOCATION: (7)..(8)

<400> SEQUENCE: 13

Cys Gly Arg Gly Asp Ser Pro Xaa
 1               5

<210> SEQ ID NO 14
<211> LENGTH: 8
<212> TYPE: PRT
<213> ORGANISM: Artificial Sequence
<220> FEATURE:
<223> OTHER INFORMATION: synthetic cyclic peptide

<400> SEQUENCE: 14

Cys Gly Arg Gly Asp Ser Pro Lys
 1               5

<210> SEQ ID NO 15
<211> LENGTH: 5
<212> TYPE: PRT
<213> ORGANISM: Artificial Sequence
<220> FEATURE:
<223> OTHER INFORMATION: synthetic cyclic peptide
<220> FEATURE:
<221> NAME/KEY: VARIANT
<222> LOCATION: (4)
<223> OTHER INFORMATION: Phe is D-Phe

<400> SEQUENCE: 15

Arg Gly Asp Phe Cys
 1               5

<210> SEQ ID NO 16
<211> LENGTH: 5
<212> TYPE: PRT
<213> ORGANISM: Artificial Sequence
<220> FEATURE:
<223> OTHER INFORMATION: synthetic cyclic peptide
<220> FEATURE:
<221> NAME/KEY: VARIANT
<222> LOCATION: (4)
<223> OTHER INFORMATION: Phe is D-Phe

<400> SEQUENCE: 16

Arg Gly Asp Phe Lys
 1               5

<210> SEQ ID NO 17
<211> LENGTH: 5
<212> TYPE: PRT
<213> ORGANISM: Artificial Sequence
<220> FEATURE:
<223> OTHER INFORMATION: synthetic cyclic peptide
```

```
<220> FEATURE:
<221> NAME/KEY: VARIANT
<222> LOCATION: (4)
<223> OTHER INFORMATION: Phe is D-Phe
<220> FEATURE:
<221> NAME/KEY: VARIANT
<222> LOCATION: (5)
<223> OTHER INFORMATION: epsilon amino group of the lysine is
      coupled with PEG

<400> SEQUENCE: 17

Arg Gly Asp Phe Lys
  1               5

<210> SEQ ID NO 18
<211> LENGTH: 5
<212> TYPE: PRT
<213> ORGANISM: Artificial Sequence
<220> FEATURE:
<223> OTHER INFORMATION: synthetic cyclic peptide
<220> FEATURE:
<221> NAME/KEY: VARIANT
<222> LOCATION: (4)
<223> OTHER INFORMATION: Phe is D-Phe
<220> FEATURE:
<221> NAME/KEY: VARIANT
<222> LOCATION: (5)
<223> OTHER INFORMATION: epsilon amino group of lysine is coupled to
      thioacetyl group

<400> SEQUENCE: 18

Arg Gly Asp Phe Lys
  1               5

<210> SEQ ID NO 19
<211> LENGTH: 5
<212> TYPE: PRT
<213> ORGANISM: Artificial Sequence
<220> FEATURE:
<223> OTHER INFORMATION: synthetic cyclic peptide
<220> FEATURE:
<221> NAME/KEY: VARIANT
<222> LOCATION: (5)
<223> OTHER INFORMATION: epsilon amino group of lysine is coupled with
      DSPE
<220> FEATURE:
<221> NAME/KEY: VARIANT
<222> LOCATION: (4)
<223> OTHER INFORMATION: Tyr is D-tyrosine residue.

<400> SEQUENCE: 19

Arg Gly Asp Tyr Lys
  1               5

<210> SEQ ID NO 20
<211> LENGTH: 5
<212> TYPE: PRT
<213> ORGANISM: Artificial Sequence
<220> FEATURE:
<223> OTHER INFORMATION: synthetic cyclic peptide
<220> FEATURE:
<221> NAME/KEY: VARIANT
<222> LOCATION: (4)
<223> OTHER INFORMATION: Tyr is D-tyrosine residue.

<400> SEQUENCE: 20

Arg Gly Asp Tyr Lys
  1               5
```

```
<210> SEQ ID NO 21
<211> LENGTH: 5
<212> TYPE: PRT
<213> ORGANISM: Artificial Sequence
<220> FEATURE:
<223> OTHER INFORMATION: synthetic cyclic peptide
<220> FEATURE:
<221> NAME/KEY: VARIANT
<222> LOCATION: (5)
<223> OTHER INFORMATION: epsilon amino group of lysine is coupled with
      DSPE-PEG moiety
<220> FEATURE:
<221> NAME/KEY: VARIANT
<222> LOCATION: (4)
<223> OTHER INFORMATION: Tyr is D-tyrosine residue.

<400> SEQUENCE: 21

Arg Gly Asp Tyr Lys
 1               5

<210> SEQ ID NO 22
<211> LENGTH: 60
<212> TYPE: PRT
<213> ORGANISM: Artificial Sequence
<220> FEATURE:
<223> OTHER INFORMATION: synthetic ELP conjugated to a hydrophobic
      moiety
<220> FEATURE:
<221> NAME/KEY: VARIANT
<222> LOCATION: (1)
<223> OTHER INFORMATION: Amino terminal nitrogen is palmitoylated
<220> FEATURE:
<221> NAME/KEY: VARIANT
<222> LOCATION: (60)
<223> OTHER INFORMATION: Carboxy terminal carboxyl group is
      amidated with -NH2.
<220> FEATURE:
<221> NAME/KEY: VARIANT
<222> LOCATION: (11)..(60)
<223> OTHER INFORMATION: any one or all of the repeat unit VPGXG can
      either be present or absent
<220> FEATURE:
<221> NAME/KEY: VARIANT
<222> LOCATION: (4)..(59)
<223> OTHER INFORMATION: Xaa (4,9,14,19,24,29,34,39,44,49,54,59) is any
      amino acid except proline

<400> SEQUENCE: 22

Val Pro Gly Xaa Gly Val Pro Gly Xaa Gly Val Pro Gly Xaa Gly Val
 1               5                  10                  15

Pro Gly Xaa Gly Val Pro Gly Xaa Gly Val Pro Gly Xaa Gly Val Pro
            20                  25                  30

Gly Xaa Gly Val Pro Gly Xaa Gly Val Pro Gly Xaa Gly Val Pro Gly
        35                  40                  45

Xaa Gly Val Pro Gly Xaa Gly Val Pro Gly Xaa Gly
    50                  55                  60

<210> SEQ ID NO 23
<211> LENGTH: 60
<212> TYPE: PRT
<213> ORGANISM: Artificial Sequence
<220> FEATURE:
<223> OTHER INFORMATION: synthetic elastin-like polypeptide sequence
      modified with stearoylation and amidation
<220> FEATURE:
<221> NAME/KEY: VARIANT
<222> LOCATION: (1)
<223> OTHER INFORMATION: Amino terminal nitrogen is stearoylated
```

<220> FEATURE:
<221> NAME/KEY: VARIANT
<222> LOCATION: (60)
<223> OTHER INFORMATION: Carboxy terminal carboxy group is amidated
      with -NH2
<220> FEATURE:
<221> NAME/KEY: VARIANT
<222> LOCATION: (4)..(59)
<223> OTHER INFORMATION: Xaa (4,9,14,19,24,29,34,39,44,49,54,59) is
      any amino acid except proline

<400> SEQUENCE: 23

Val Pro Gly Xaa Gly Val Pro Gly Xaa Gly Val Pro Gly Xaa Gly Val
 1               5                  10                  15

Pro Gly Xaa Gly Val Pro Gly Xaa Gly Val Pro Gly Xaa Gly Val Pro
            20                  25                  30

Gly Xaa Gly Val Pro Gly Xaa Gly Val Pro Gly Xaa Gly Val Pro Gly
        35                  40                  45

Xaa Gly Val Pro Gly Xaa Gly Val Pro Gly Xaa Gly
    50                  55                  60

<210> SEQ ID NO 24
<211> LENGTH: 60
<212> TYPE: PRT
<213> ORGANISM: Artificial Sequence
<220> FEATURE:
<223> OTHER INFORMATION: synthetic elastin-like polypeptide sequence
      wherein the n is 12.
<220> FEATURE:
<221> NAME/KEY: VARIANT
<222> LOCATION: (4)..(59)
<223> OTHER INFORMATION: Xaa (4,9,14,19,24,29,34,39,44,49,54,59) is
      any amino acid except proline

<400> SEQUENCE: 24

Val Pro Gly Xaa Gly Val Pro Gly Xaa Gly Val Pro Gly Xaa Gly Val
 1               5                  10                  15

Pro Gly Xaa Gly Val Pro Gly Xaa Gly Val Pro Gly Xaa Gly Val Pro
            20                  25                  30

Gly Xaa Gly Val Pro Gly Xaa Gly Val Pro Gly Xaa Gly Val Pro Gly
        35                  40                  45

Xaa Gly Val Pro Gly Xaa Gly Val Pro Gly Xaa Gly
    50                  55                  60

<210> SEQ ID NO 25
<211> LENGTH: 60
<212> TYPE: PRT
<213> ORGANISM: Artificial Sequence
<220> FEATURE:
<223> OTHER INFORMATION: synthetic elastin-like polypeptide sequence
      wherein the m is 12.
<220> FEATURE:
<221> NAME/KEY: VARIANT
<222> LOCATION: (5)..(60)
<223> OTHER INFORMATION: Xaa (5, 10, 15, 20, 25, 30, 35, 40, 45, 50,
      55, 60) is any amino acid except proline

<400> SEQUENCE: 25

Gly Val Pro Gly Xaa Gly Val Pro Gly Xaa Gly Val Pro Gly Xaa Gly
 1               5                  10                  15

Val Pro Gly Xaa Gly Val Pro Gly Xaa Gly Val Pro Gly Xaa Gly Val
            20                  25                  30

```
Pro Gly Xaa Gly Val Pro Gly Xaa Gly Val Pro Gly Xaa Gly Val Pro
        35                  40                  45

Gly Xaa Gly Val Pro Gly Xaa Gly Val Pro Gly Xaa
    50                  55                  60

<210> SEQ ID NO 26
<211> LENGTH: 30
<212> TYPE: PRT
<213> ORGANISM: Artificial Sequence
<220> FEATURE:
<223> OTHER INFORMATION: synthetic ELP conjugated to a hydrophobic
      moiety
<220> FEATURE:
<221> NAME/KEY: VARIANT
<222> LOCATION: (5)..(30)
<223> OTHER INFORMATION: Xaa (5, 10, 15, 20, 25, 30) is any amino acid
      except proline
<220> FEATURE:
<221> NAME/KEY: VARIANT
<222> LOCATION: (11)..(30)
<223> OTHER INFORMATION: any one or all of amino acid repeat unit GVPGX
      present at positon 11-30 can either be present or absent
<220> FEATURE:
<221> NAME/KEY: VARIANT
<222> LOCATION: (1)
<223> OTHER INFORMATION: Amino terminal nitrogen is stearoylated

<400> SEQUENCE: 26

Gly Val Pro Gly Xaa Gly Val Pro Gly Xaa Gly Val Pro Gly Xaa Gly
 1               5                  10                  15

Val Pro Gly Xaa Gly Val Pro Gly Xaa Gly Val Pro Gly Xaa
            20                  25                  30

<210> SEQ ID NO 27
<211> LENGTH: 5
<212> TYPE: PRT
<213> ORGANISM: Artificial Sequence
<220> FEATURE:
<223> OTHER INFORMATION: synthetic cyclic peptide
<220> FEATURE:
<221> NAME/KEY: VARIANT
<222> LOCATION: (5)
<223> OTHER INFORMATION: lysine is conjugated with -R1-.
<220> FEATURE:
<221> NAME/KEY: VARIANT
<222> LOCATION: (4)
<223> OTHER INFORMATION: Tyr is D-tyrosine residue.

<400> SEQUENCE: 27

Arg Gly Asp Tyr Lys
 1               5

<210> SEQ ID NO 28
<211> LENGTH: 5
<212> TYPE: PRT
<213> ORGANISM: Artificial Sequence
<220> FEATURE:
<223> OTHER INFORMATION: synthetic Elastin like polypeptide

<400> SEQUENCE: 28

Val Pro Gly Val Gly
 1               5
```